United States Patent
Braier et al.

(10) Patent No.: US 9,782,624 B2
(45) Date of Patent: Oct. 10, 2017

(54) INTERCHANGEABLE GRIP AND PINCH STRENGTH ASSESSOR AND EXERCISER

(71) Applicant: Kiio Inc., Madison, WI (US)

(72) Inventors: Robert Braier, Fitchburg, WI (US); John McCluskey, Fitchburg, WI (US); Nicholas Ladas, Madison, WI (US); Richard Tejeda, Madison, WI (US)

(73) Assignee: Kiio Inc., Madison, WI (US)

( * ) Notice: Subject to any disclaimer, the term of this patent is extended or adjusted under 35 U.S.C. 154(b) by 44 days.

(21) Appl. No.: 15/013,894

(22) Filed: Feb. 2, 2016

(65) Prior Publication Data

US 2016/0220863 A1 Aug. 4, 2016

Related U.S. Application Data

(60) Provisional application No. 62/111,448, filed on Feb. 3, 2015.

(51) Int. Cl.
*A63B 23/16* (2006.01)
*A63B 21/055* (2006.01)
(Continued)

(52) U.S. Cl.
CPC .............. *A63B 23/16* (2013.01); *A61B 5/225* (2013.01); *A63B 21/0442* (2013.01);
(Continued)

(58) Field of Classification Search
CPC ..... A63B 23/16; A63B 21/4035; A63B 5/225; A63B 21/0442; A63B 21/0552; A63B 23/03508; A63B 21/4039; A63B 21/4045; A63B 21/00061; A63B 21/00065; A63B 21/00069; A63B 21/0023; A63B 2071/065; A63B 2071/0694; A63B 2207/02;
(Continued)

(56) References Cited

U.S. PATENT DOCUMENTS

| 3,357,702 A | 12/1967 | Van Saders |
| 3,442,132 A | 5/1969 | De Mare |

(Continued)

FOREIGN PATENT DOCUMENTS

| JP | H09313467 | 12/1997 |
| JP | 2002345794 | 12/2002 |

(Continued)

OTHER PUBLICATIONS

"TrackerFreedom® Wireless Grip," JTech Medical, jtechmedical.com, Feb. 18, 2013. https://web.archive.org/web/20130218190450/http://www.jtechmedical.com/Tracker-Freedom-Wireless-Instruments/tracker-freedom-wireless-grip.

(Continued)

*Primary Examiner* — Andrew S Lo
(74) *Attorney, Agent, or Firm* — Jennifer L. Gregor; Godfrey & Kahn, S.C.

(57) ABSTRACT

A hand strength appliance is provided that may be used in multiple or selected configurations for grip and pinch strength assessment as well as grip and pinch exercises. The appliance includes a frame and a sliding internal handle fitted within and slidable within the frame, and may be positioned for multiple test positions and exercises. The appliance may include and be used with a force sensing device that may transmit information to a computing device.

22 Claims, 22 Drawing Sheets

(51) Int. Cl.
  *A63B 23/035*  (2006.01)
  *A63B 21/04*  (2006.01)
  *A61B 5/22*  (2006.01)
  A63B 21/002  (2006.01)
  A63B 21/00  (2006.01)
  A63B 71/06  (2006.01)
  A61B 5/00  (2006.01)
  G06Q 10/06  (2012.01)

(52) U.S. Cl.
  CPC ...... *A63B 21/0552* (2013.01); *A63B 21/4035* (2015.10); *A63B 23/03508* (2013.01); *A61B 5/4833* (2013.01); *A63B 21/0023* (2013.01); *A63B 21/00061* (2013.01); *A63B 21/00065* (2013.01); *A63B 21/00069* (2013.01); *A63B 21/4039* (2015.10); *A63B 21/4045* (2015.10); *A63B 2071/065* (2013.01); *A63B 2071/0694* (2013.01); *A63B 2207/02* (2013.01); *A63B 2220/51* (2013.01); *A63B 2225/20* (2013.01); *A63B 2225/50* (2013.01); *G06Q 10/0639* (2013.01)

(58) Field of Classification Search
  CPC ............ A63B 2220/51; A63B 2225/20; A63B 2225/50; A63B 21/055; A63B 21/0555; A63B 21/0557; A61B 5/4833; G06Q 10/0639
  USPC .................................................. 482/8, 44–49
  See application file for complete search history.

(56) References Cited

U.S. PATENT DOCUMENTS

| | | | |
|---|---|---|---|
| 3,570,849 A | 3/1971 | Ratchford | |
| 3,670,573 A | 6/1972 | Kroemer | |
| 3,672,219 A | 6/1972 | Van Patten | |
| 4,226,412 A | 10/1980 | Panepinto | |
| 4,553,746 A * | 11/1985 | Lee | A63B 21/05 482/49 |
| 4,674,330 A | 6/1987 | Ellis | |
| 4,882,677 A | 11/1989 | Curran | |
| 4,884,445 A | 12/1989 | Sadoff | |
| 4,922,925 A | 5/1990 | Crandall | |
| 4,939,933 A * | 7/1990 | Curran | A61B 5/103 482/8 |
| 4,949,729 A | 8/1990 | Haski | |
| 5,125,878 A * | 6/1992 | Wingate | A63B 23/16 482/121 |
| 5,163,443 A | 11/1992 | Fry-Welch et al. | |
| D353,859 S * | 12/1994 | Grey | D21/684 |
| 5,445,582 A | 8/1995 | Brown | |
| 5,611,755 A * | 3/1997 | Blackmore | A63B 23/16 482/126 |
| 5,723,785 A | 3/1998 | Manning | |
| 6,007,460 A * | 12/1999 | Young | A63B 21/0004 482/121 |
| D429,782 S * | 8/2000 | Grey | D21/684 |
| 6,443,874 B1 | 9/2002 | Bennett | |
| 6,497,641 B1 | 12/2002 | Hinds | |
| 6,678,549 B2 | 1/2004 | Cusimano | |
| 6,923,750 B1 | 8/2005 | Hinds | |
| 7,010,835 B2 * | 3/2006 | Tillim | A61B 17/00 16/110.1 |
| 7,824,312 B1 * | 11/2010 | Hsu | A63B 23/16 482/108 |
| 8,082,786 B1 | 12/2011 | Akins | |
| 8,491,446 B2 | 7/2013 | Hinds | |
| 8,491,466 B2 | 7/2013 | Okada | |
| 8,601,869 B2 | 12/2013 | Miller | |
| 9,171,131 B2 | 10/2015 | Meyer | |
| 2007/0042881 A1 * | 2/2007 | Wu | A63B 21/0004 482/126 |
| 2012/0143064 A1 | 6/2012 | Cyphery | |
| 2012/0255355 A1 | 10/2012 | Xu | |
| 2012/0302406 A1 * | 11/2012 | Hinds | A63B 21/0055 482/8 |
| 2013/0288864 A1 * | 10/2013 | Holland | A63B 21/4023 482/126 |
| 2014/0038785 A1 * | 2/2014 | Silagy | A63B 23/16 482/47 |
| 2014/0205980 A1 | 7/2014 | Braier | |
| 2014/0323271 A1 | 10/2014 | Hinds et al. | |
| 2015/0045186 A1 * | 2/2015 | Ranky | A63B 23/16 482/8 |
| 2015/0133278 A1 | 5/2015 | Braier | |
| 2015/0141215 A1 * | 5/2015 | Williams | A63B 21/0552 482/124 |
| 2015/0170532 A1 | 6/2015 | Yancosek | |

FOREIGN PATENT DOCUMENTS

| | | |
|---|---|---|
| JP | 2006340795 | 12/2006 |
| WO | WO2011036350 | 3/2011 |

OTHER PUBLICATIONS

"H500 Hand Kit," Biometrics Ltd., biometricsltd.com, Sep. 17, 2013. https://web.archive.org/web/20130917163532/http://www.biometricsltd.com/h500.htm.
"Jamar Hydraulic Dynamometer," QuickMedical®, quickmedical.com, Nov. 7, 2013. https://web.archive.org/web/20131107153245/http://www.quickmedical.com/fabricationenterprises-jamar-hydraulic-dynamometer.html.
"Fitness Testing: Handgrip Strength Test," Top End Sports, topendsports.com, Feb. 17, 2012. https://web.archive.org/web/20120217111959/http://www.topendsports.com/testing/tests/handgrip.htm.
Spring Grip: http://www.dickssportinggoods.com/product/index.jsp?productId=22950676; Feb. 26, 2016.
Gripmaster: http://www.amazon.com/Gripmaster-Hand-Exerciser/dp/B0085MX3SG; Feb. 26, 2016.
Norco Hand Exerciser: http://www.amazon.com/Norco-Rainbow-Hand-Exerciser-Ib/dp/B0052ZTQPI/ref=sr_1_2?s=hpc&ie=UTF8&qid=1455015463&sr=1-2&keywords=norco+hand+exerciser; Feb. 26, 2016.
Rolyan Basic Ergonomic Hand Exerciser: http://www.amazon.com/Basic-Ergonomic-Hand-Exerciser-Rolyan/dp/B002BV269Y; Feb. 26, 2016.
Cando Adjustable 6-Spring Hand Grip: http://www.amazon.com/Cando-10-0801-CanDo-6-Spring-Hand/dp/B001RQ0FDI; Feb. 26, 2016.
Camry Digital: http://www.amazon.com/Digital-Dynamometer-Strength-Measurement-Capturing/dp/B00A8K4L84; Feb. 26, 2016.
Jamar Hydraulic: http://www.amazon.com/Fabrication-12-0600-Jamar-Hydraulic-Dynamometer/dp/B00081G60Y; Feb. 26, 2016.
Jamar Plus+ Digital: http://www.amazon.com/Jamar-Plus-digital-dynamometer-200Ib/dp/B002BUJ3QE; Feb. 26, 2016.
Bosch K-MAP: http://www.bosche.eu/en/products/medical-scales/hand-grip-dynamometer-k-map; Feb. 26, 2016.
DynEx: http://www.prohealthcareproducts.com/dynx1-electronic-hand-dynamometer-grip-strength-endurance-tester/; Feb. 26, 2016.
Smedley III: http://www.amazon.com/SMEDLEY-ANALOG-STRENGTH-TESTER-T-18/dp/B001ETZPXS; Feb. 26, 2016.

* cited by examiner

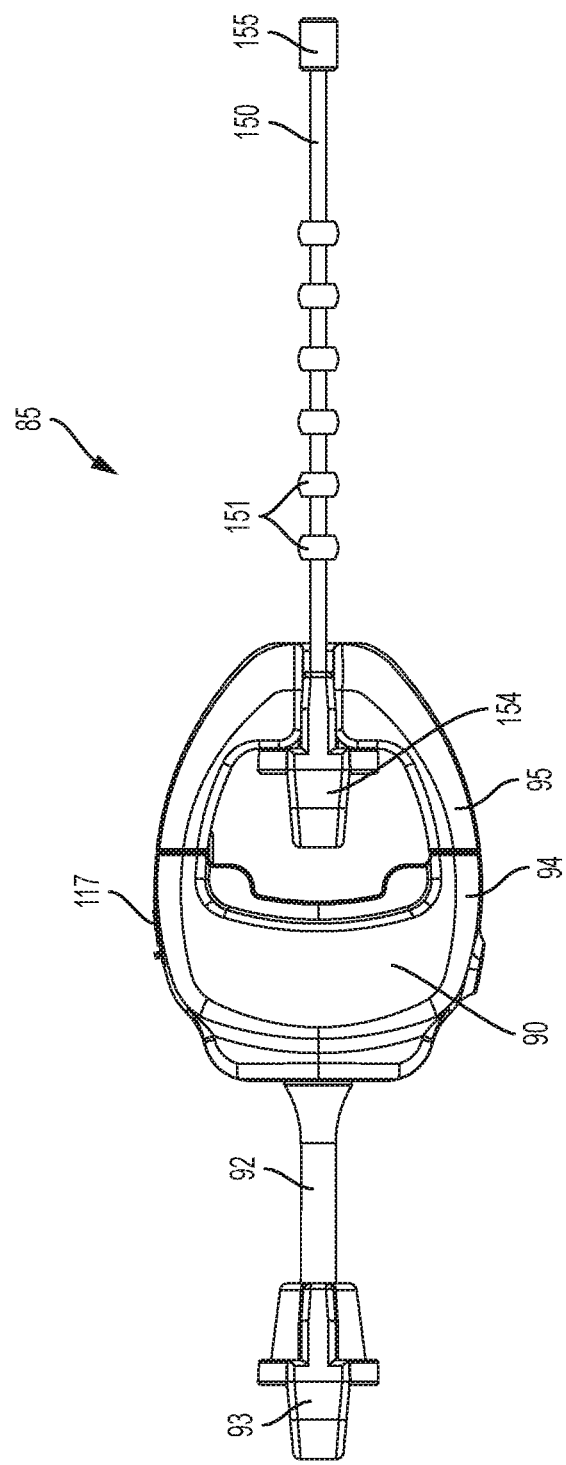

(Test Position 1)

(Test Position 2)

(Test Position 3)

(Test Position 4)

(Test Position 5)

(Test Position "P")

(Test Position "P")

(Test Position 1)

(Test Position 2)

(Test Position 3)

(Test Position 4)

(Test Position 5)

INTERCHANGEABLE GRIP AND PINCH STRENGTH ASSESSOR AND EXERCISER

CROSS REFERENCE TO RELATED APPLICATIONS

This application claims the benefit of U.S. Provisional Patent Application Ser. No. 62/111,448, filed on Feb. 3, 2015, the disclosure of which is incorporated by reference herein in its entirety for all purposes.

FIELD OF THE INVENTION

The present invention relates generally to the fields of exercise devices and therapy assessment. More particularly, the present invention relates to devices for grip and pinch strength assessment and exercising.

BACKGROUND

Hand strength, including both grip strength and pinch strength, is important for daily life function and may be important in certain sports as well. Athletic training programs as well as therapy rehabilitation regimens following injury or surgery may target grip strength, pinch strength, or both. Athletic trainers, coaches, physical therapists and occupational therapists need to assess current strength capabilities, as well as to prescribe exercises to increase strength and to track progress and adherence during the course of training or rehabilitation. The inventions and devices disclosed here offer several advantages over current grip and pinch exercisers and assessors.

A number of grip exercising products currently exist that are designed to strengthen the hand and forearm muscles, including for example, the Spring Grip, Gripmaster, Norco Hand Exerciser, Rolyan Basic Ergonomic Hand Exerciser, and Cando Adjustable 6-Spring Hand Grip devices. Separate from grip exercising products, a category of grip assessment products exist for measuring grip strength, including, for example the Camry Digital, Jamar Hydraulic, Jamar Plus+ Digital, Bosch K-MAP, DynEx, and SMEDLEY III. Additionally, the inventors are not aware of any commercial devices in which the capability is provided for live or real-time data feedback. The inventions disclosed and claimed here constitute significant improvements over the prior art devices, providing useful and efficient exercising and assessment capabilities for both grip strength and pinch strength, all in one product.

It will be understood by those skilled in the art that one or more aspects of these inventions can meet certain objectives, while one or more there aspects can lead to certain other objectives. Other objects, features, benefits and advantages of the present inventions will be apparent in this summary and descriptions of the disclosed embodiment, and will be readily apparent to those skilled in the art. Such objects, features, benefits and advantages will be apparent from the above as taken in conjunction with the accompanying figures and all reasonable inferences to be drawn therefrom.

SUMMARY OF THE INVENTION

A multiple configuration hand assessment and exercising appliance includes: a frame having a connector end with a connector socket, a handle end, and a channel on the interior surface of the frame; an internal handle having a bar and two sliding portions, the internal handle fitted within the frame and slidable within the channel; a stabilizing member adjustably connected to the two sliding portions, the stabilizing member including a stabilizing socket for positioning the bar with respect to the handle end of the frame to provide multiple test positions; and a force sensor assembly secured within the connector socket on the connector end of the frame and within the stabilizing socket, the force sensor assembly being capable of processing and transmitting force measurement data to a computing device.

A hand strength appliance includes: a frame having arms; a handle end, an interior surface, and a connector end including a connector socket; an internal handle fitted within the frame and slidable within the interior surface of the frame, the internal handle including a bar and two sliding portions that are operably connected to the bar and together slide within the interior surface of the frame; a stabilizing member adjustably connected to the two sliding portions, the stabilizing member including a stabilizing socket for positioning the bar with respect to the handle end of the frame to provide multiple test positions; and the appliance is capable of receiving and securing one or more removable resistance elements within the connector socket and the stabilizing socket.

A method for assessing grip strength at multiple test positions including the steps of: providing an appliance set to a first test position, the appliance including a frame having a connector end, a handle end, and a channel on the interior surface of the frame; an internal handle fitted within the frame and slidable within the channel, the internal handle including a bar operably connected to two sliding portions of the internal handle; a stabilizing member adjustably connected to the two sliding portions, the stabilizing member including a stabilizing socket for receiving a resistance element for positioning the bar with respect to the handle end of the frame to provide multiple test positions; a force sensor assembly secured within a connector socket on the connector end of the frame and within the stabilizing socket; the force sensor assembly capable of processing and transmitting force measurement data to a computing device; measuring the isometric force from a user squeezing the bar towards the handle end of the appliance in the first test position, resulting in first test position data; adjusting the appliance by changing the position of the stabilizing member relative to the handle end of the frame to provide a second test position; measuring the isometric force from the user squeezing the bar towards the handle end of the appliance in the second test position, resulting in second test position data; and communicating the first test position data and the second test position data to a computing device.

BRIEF DESCRIPTION OF THE DRAWINGS

FIG. 10A is an elevation view of a force sensor assembly in accordance with the invention.

Figure 26:
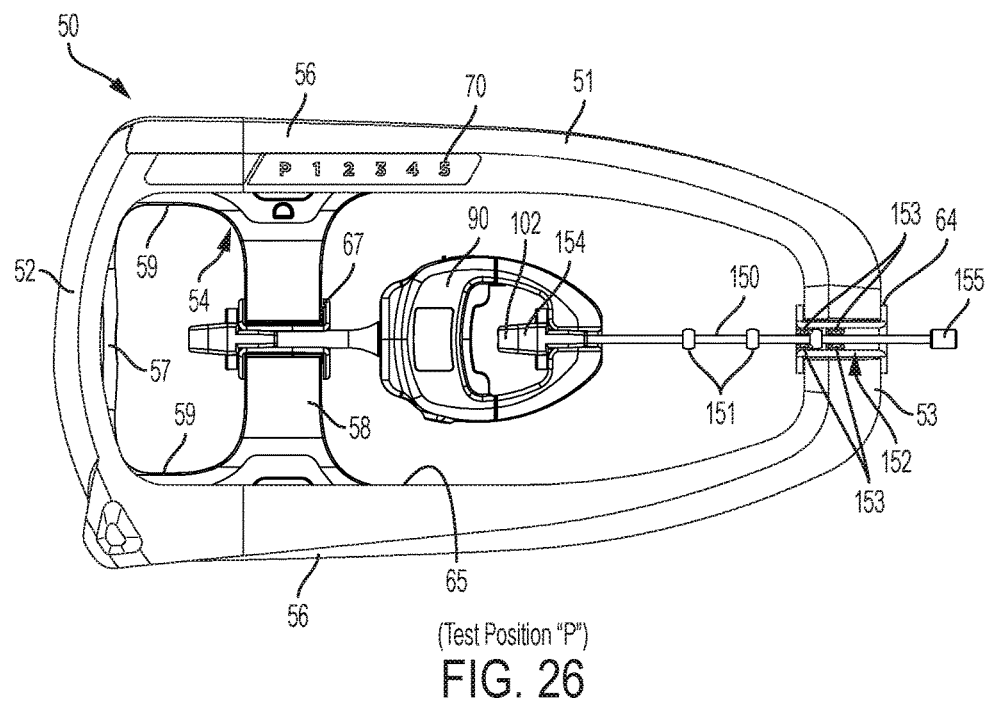
FIG. 26 is an elevation view of an appliance in accordance with the invention showing the appliance set for a pinch test position.
Figure 27:
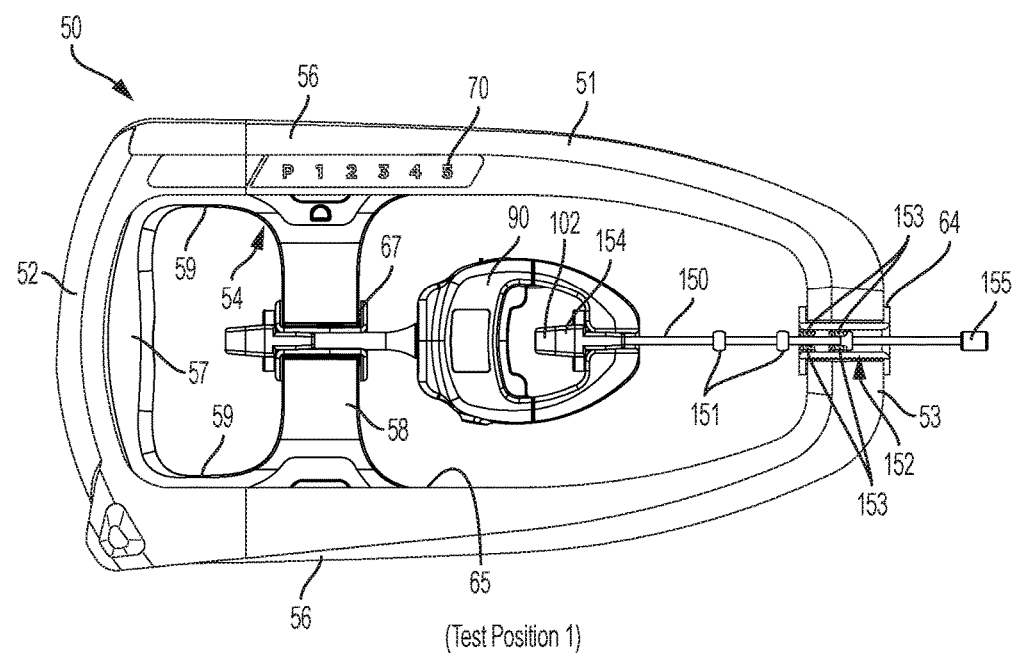
FIG. 27 is an elevation view of the appliance in FIG. 26 showing the appliance set for a first test position.
Figure 28:
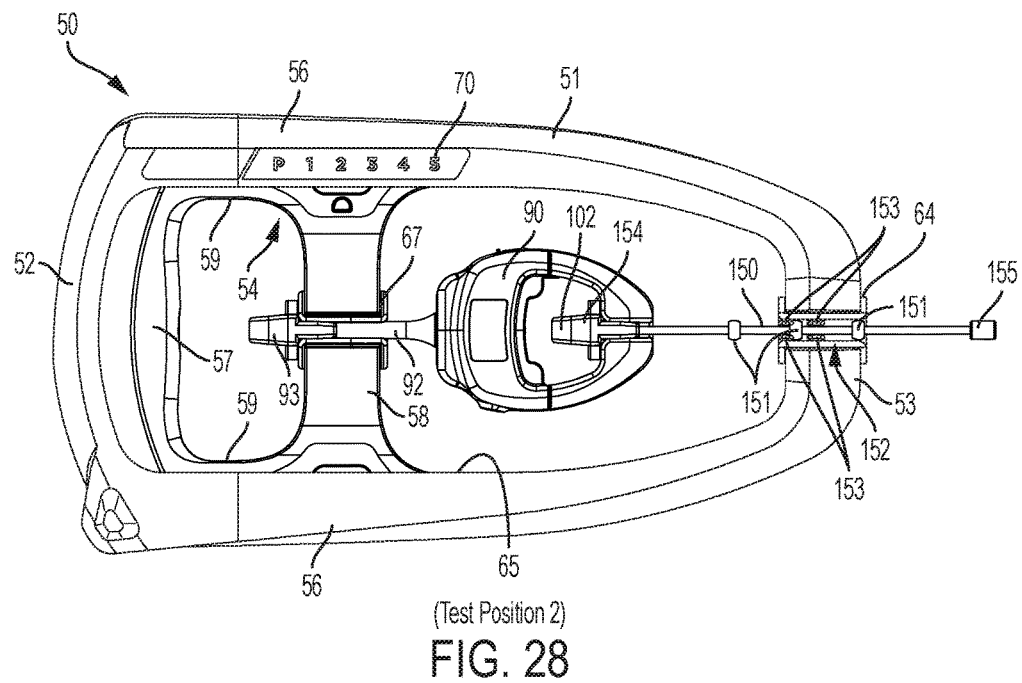
FIG. 28 is an elevation view of the appliance in FIG. 26 showing the appliance set for a second test position.
Figure 29:
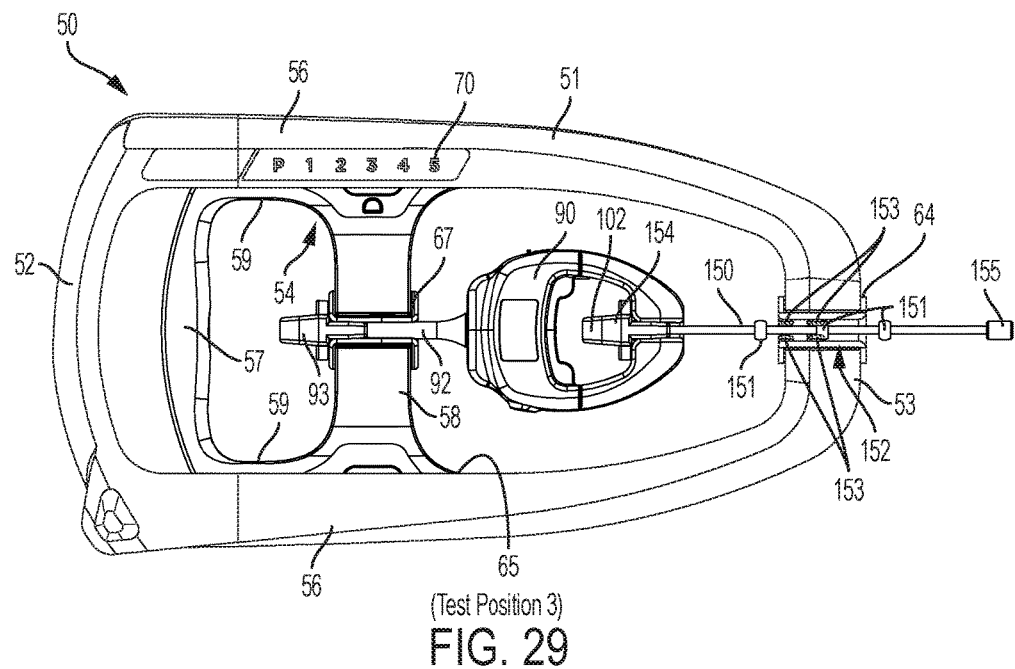
FIG. 29 is an elevation view of the appliance in FIG. 26 showing the appliance set for a third test position.
Figure 30:
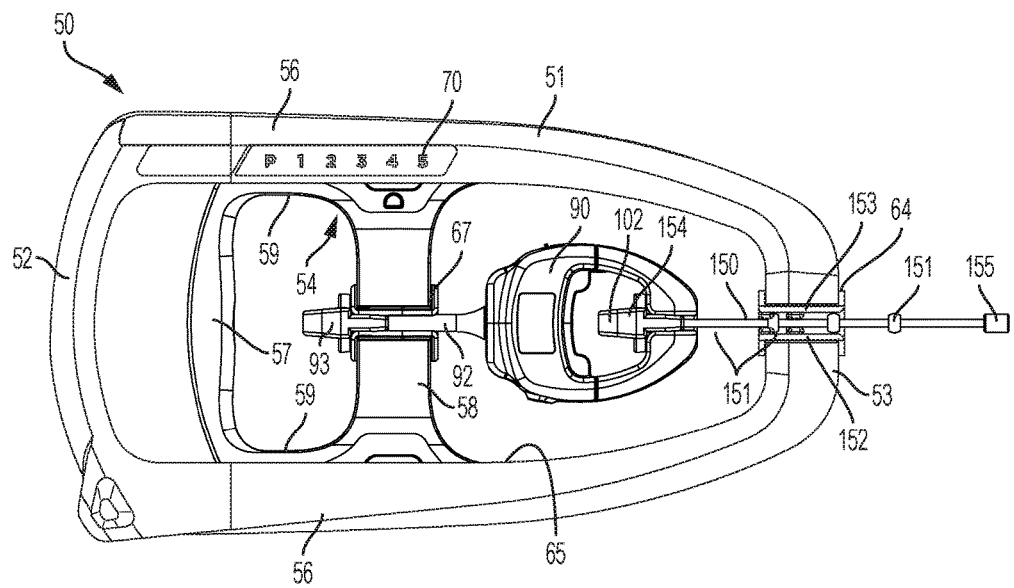

FIG, 30 is an elevation view of the appliance in FIG. 26 showing the appliance set for a fourth test position.

Figure 31:
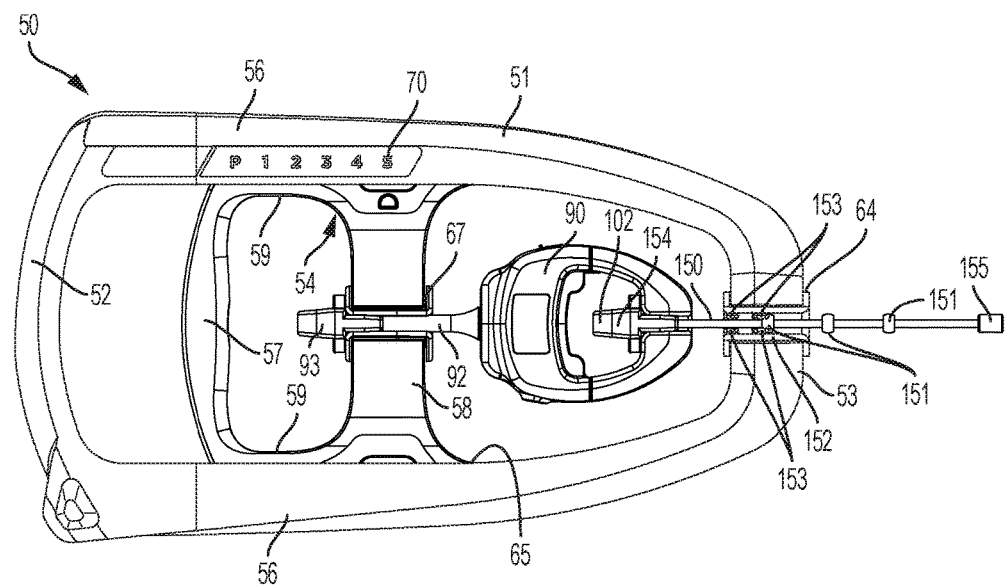

FIG. 31 is an elevation view of the appliance in FIG. 26 showing the appliance set for a fifth test position.

DETAILED DESCRIPTION

Figure 1:
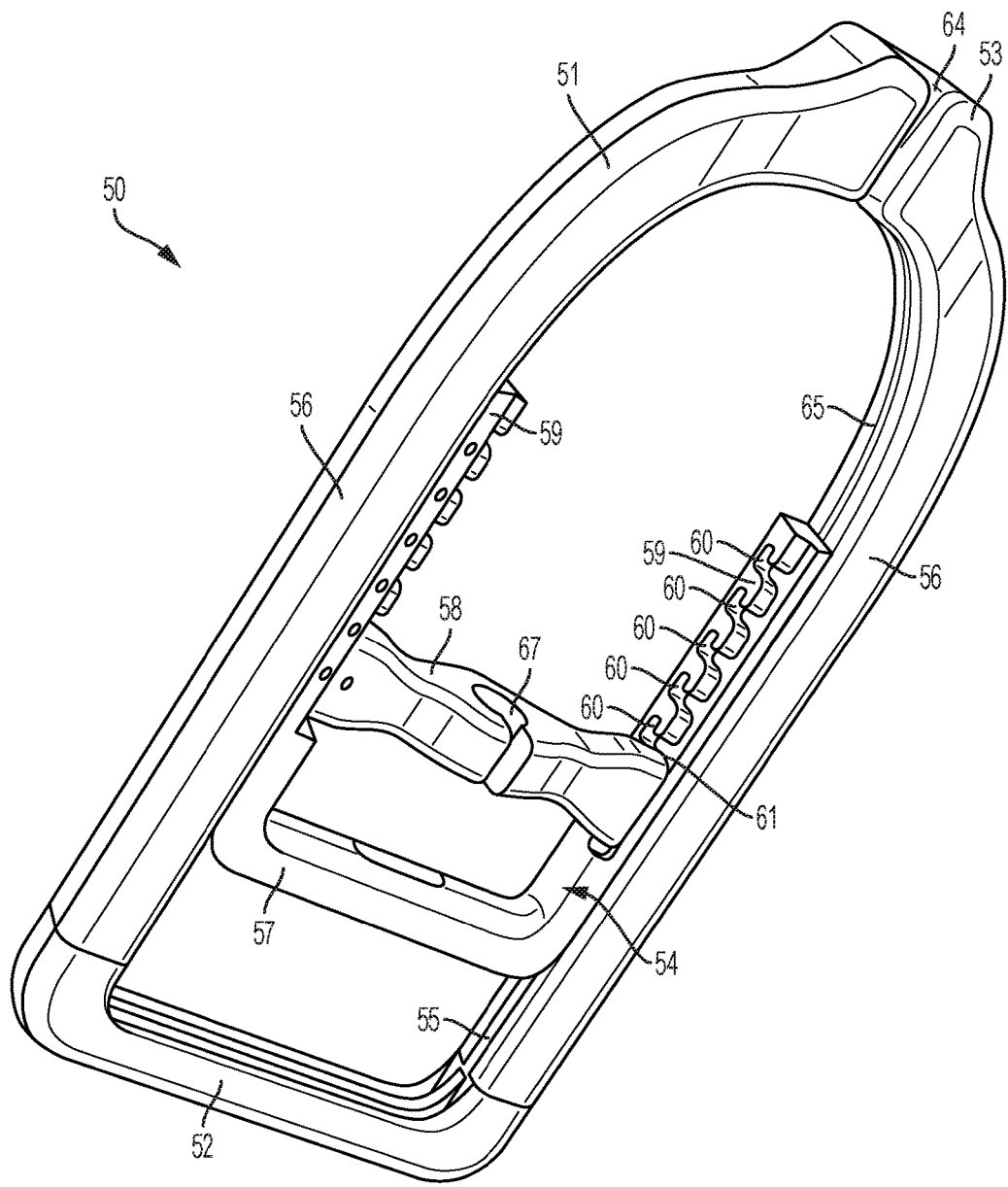
FIG. 1 is an isometric view of one embodiment of an appliance in accordance with the present invention.
Figure 2:
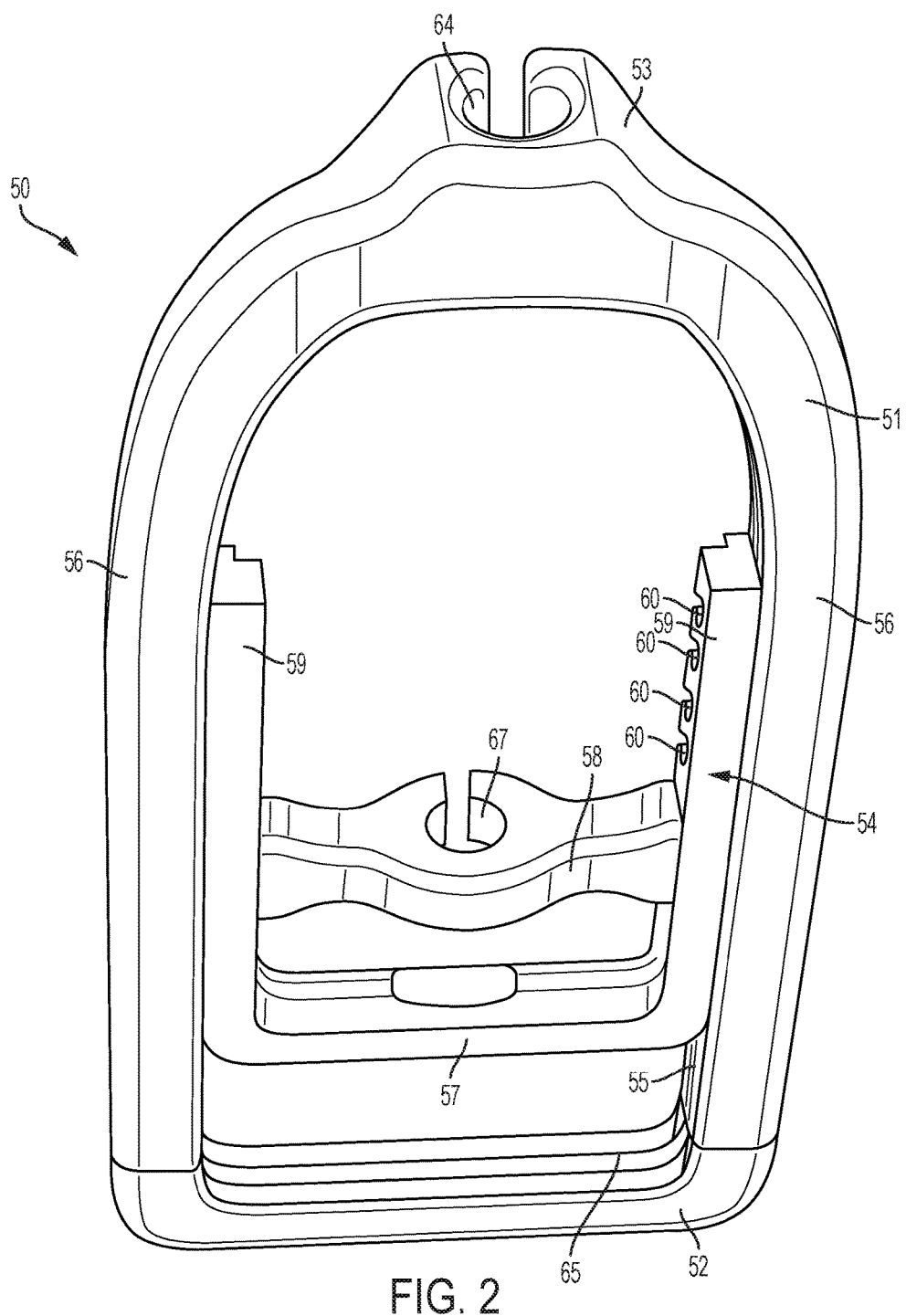
FIG. 2 is an isometric view showing the reverse side view of the appliance of FIG.
Figure 3:
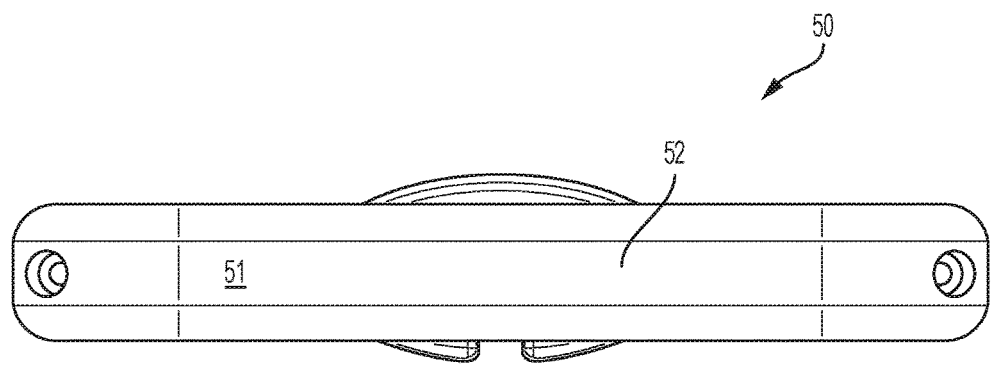
FIG. 3 is an end elevation view showing the handle end of the appliance of FIG.
Figure 4:
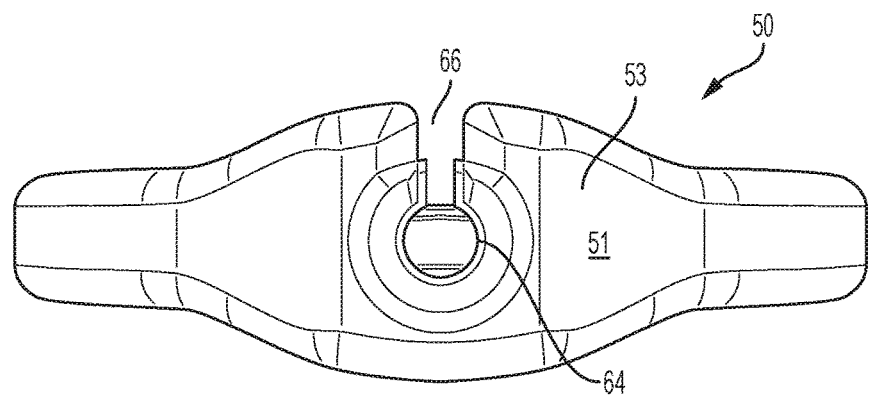
FIG. 4 is an end elevation view of the connector end of the appliance of FIG. 1.

FIGS. 1-4 show one embodiment of an appliance 50 that may be used in multiple configurations as a hand assessment device, a hand exercising device, or both. As used herein, the terms "hand strength assessment," "hand assessment," "hand testing," and the like should be understood to refer to both grip strength testing and pinch strength testing. Similarly, "hand" exercises should be understood to include both grip and pinch exercises. As shown in the drawings, appliance 50 includes a frame 51, having a handle end 52 and a connector end 53. The appliance 50 also has an internal handle 54, which is engaged within and slides within frame 51. In the embodiment shown in FIGS. 1-4, internal handle 54 slides within a channel 55 on the interior of the arms 56 of the frame 51. Other sliding engagement structures and relationships may be used instead of a channel, such as a groove, recess, slots, or dowel rails engaged with slides. Internal handle 54 includes bar 57, stabilizing member 58, and sliding portions 59. In sonic embodiments, for example as shown in FIGS. 1 and 2, the stabilizing member 58 may be adjustable. These two figures show an embodiment in which stabilizing member 58 is adjustable by way of changing the position of stabilizing member 58 with respect to niches 60 in the sliding portions 59 of the internal handle 54. Stabilizing member 58 has notched ends 61 (see FIG. 9) that correspond to niches 60 and also includes a stabilizing socket 67. FIG. 3 shows the handle end 52 of frame 51; FIG. 4 shows the connector end 53 of frame 51, including connector slot 66 in connector socket 64. The appliance 50 is capable of receiving and securing one or more removable resistance elements within the connector socket 64 and the stabilizing socket 67. As explained below, resistance elements may include a number of devices or assemblies alone or in combination, including for example, a force sensor assembly 85, a force sensing device 90, an elastic member, resistance cables e.g., 140, 141, 144), anchoring inserts for testing (e.g. positioning cables 150 or anchoring inserts 120), or other devices and assemblies providing anchoring or resistance within the appliance.

A variety of materials may be used for the components of an appliance 50 in accordance with the invention. It will be apparent to one of skill in the art that certain types of plastics may be too flexible to be useful for strength assessment because they will deform when the force applied exceeds a certain level. Appropriate materials would include those that will resist deforming or pliability when used as contemplated here, including, for example, glass-filled nylon or metal.

Figure 5:
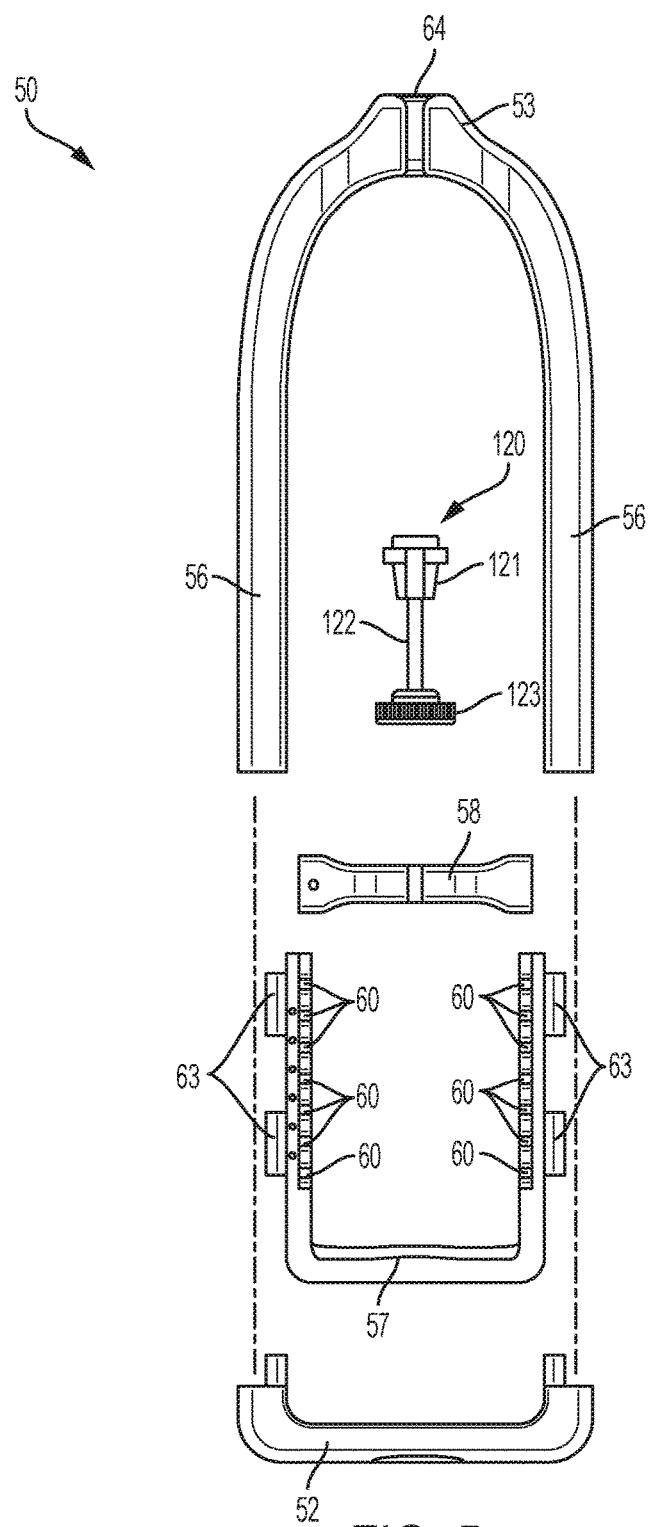
FIG. 5 is an exploded elevation view of the appliance shown in FIG. 1.

As shown in FIG. 5, the frame 51 may include the channel 55 within which the sliding portions 59 of the internal handle 54 slide. In one embodiment, assembly of the appliance 50 may include inserting the internal handle 54 within the channel 55 of arms 56, and then attaching the handle end 52 in a manner such that the various portions or components of the frame 51 remain assembled and secure during use. As shown in FIG. 5, internal handle 54 may also have fins 63 to help guide the internal handle 54 within the channel 55.

Other ways of assembling the appliance 50 will be apparent to those of ordinary skill in the art, and are included within the scope of the invention.

Figure 6:
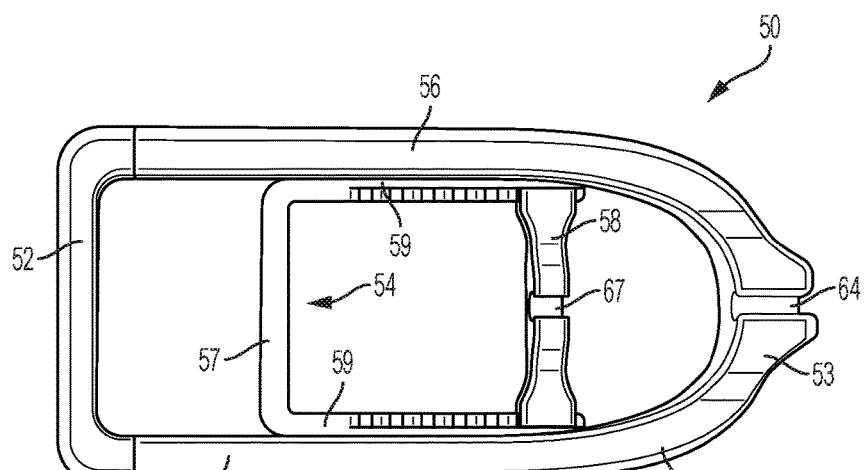
FIG. 6 is an elevation view of an appliance in accordance with the invention showing the handle in a position closest to the connector end of the appliance.
Figure 7:
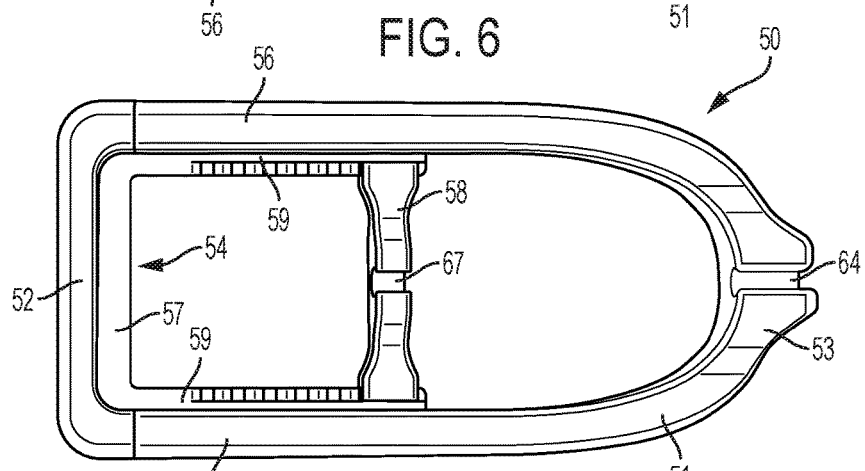
FIG. 7 is an elevation view of the appliance in FIG. 6, showing the handle in a position closest to the handle end of the appliance.
Figure 8:
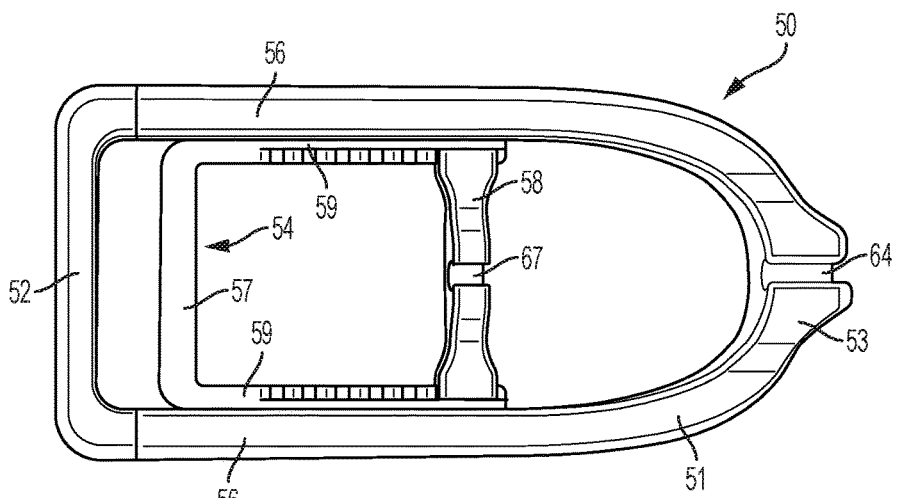
FIG. 8 is an elevation view of the appliance in FIG. 6, showing the handle in a position intermediate to the positions shown in FIG. 6 and FIG. 7.

FIGS. 6-8 illustrate the sliding capability of internal handle 54 within a frame 51. FIG. 6 shows an appliance 50 with internal handle 54 in a position closest to the connector end 53 of the appliance 50. FIG. 7 shows the internal handle 54 in a position closest to the handle end 52. FIG. 8 shows the internal handle 54 in an intermediate position. The range of sliding motion of internal handle 54 will vary depending on the space allowed for sliding in a particular embodiment, but depending on the functions desired in a given embodiment, should allow for enough motion and variability for the desired functions of testing and exercise for both grip strength and pinch strength.

Figure 9A:
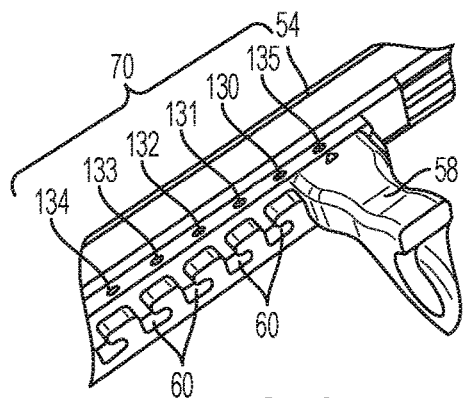
FIG. 9A is a perspective view of a portion of an internal handle in accordance with the invention, showing the stabilizing member secured within niches at a pinch test position.
Figure 9B:
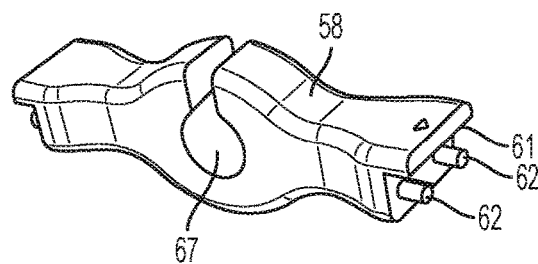
FIG. 9B is a perspective view of the stabilizing member of FIG. 9A showing the notched ends and pegs.
Figure 9C:
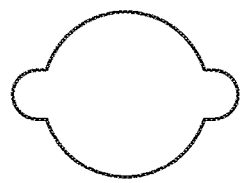
FIG. 9C shows an alternative attachment structure for attaching the stabilizing member to the internal handle of an appliance.

As noted above, the stabilizing member 58 may be adjustable. In one embodiment shown in FIGS. 9A and 9B, stabilizing member 58 may be inserted into one of six different niches 60 in the sliding portions 59 of an internal handle 54. A stabilizing member 58 may include pegs 62 on notched ends 61 that may be positioned within niches 60 by inserting the pegs 62 into the niches 60 and then sliding the stabilizing member 58 to secure it within the internal handle 54. Alternatively, an alternative attachment structure could incorporate a single peg with a biased shape inserted into a corresponding hole as shown in FIG. 9C. Numerous other mechanical connections could be used, such as a hook and latch system, numerous other peg configurations, or other snapping and fitting mechanisms. The removal and insertion of the stabilizing member 58 is designed to be done by the end user, with the goal of either increasing or decreasing the gap between the handle end 52 of the appliance 50 and the bar 57 of the internal handle 54 to accommodate different hand or testing positions. There may be markings 70 on the frame 51 or internal handle 54 to aid in the placement of the stabilizing member 58. In FIG. 9a these are labeled: 1, 2, 3, 4, 5, and P, which correspond to the five common or standard grip testing positions as well as the "P" for a pinch test position. More or less markings 70 and more or less positions could be incorporated into the design within the spirit of the invention. One purpose of the markings 70 is to create repeatable and accurate spacing options when doing assessments. This basic conceptual design thus provides an interchangeable and adjustable appliance 50 that can be used in several different configurations, which are described by way of example in more detail below.

Figure 10:
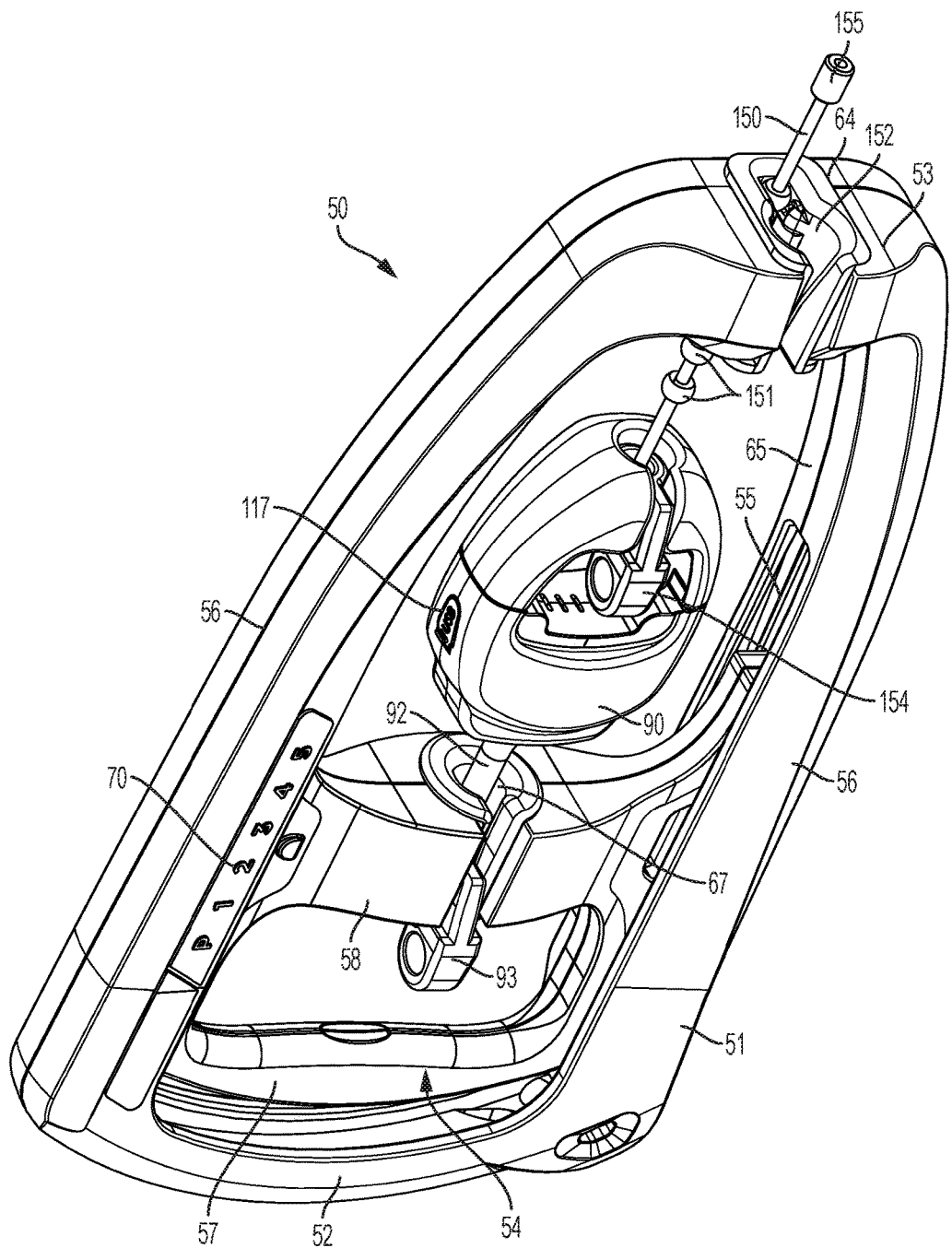
FIG. 10 is an isometric view of another embodiment of an appliance in accordance with the present invention.
Figure 11:
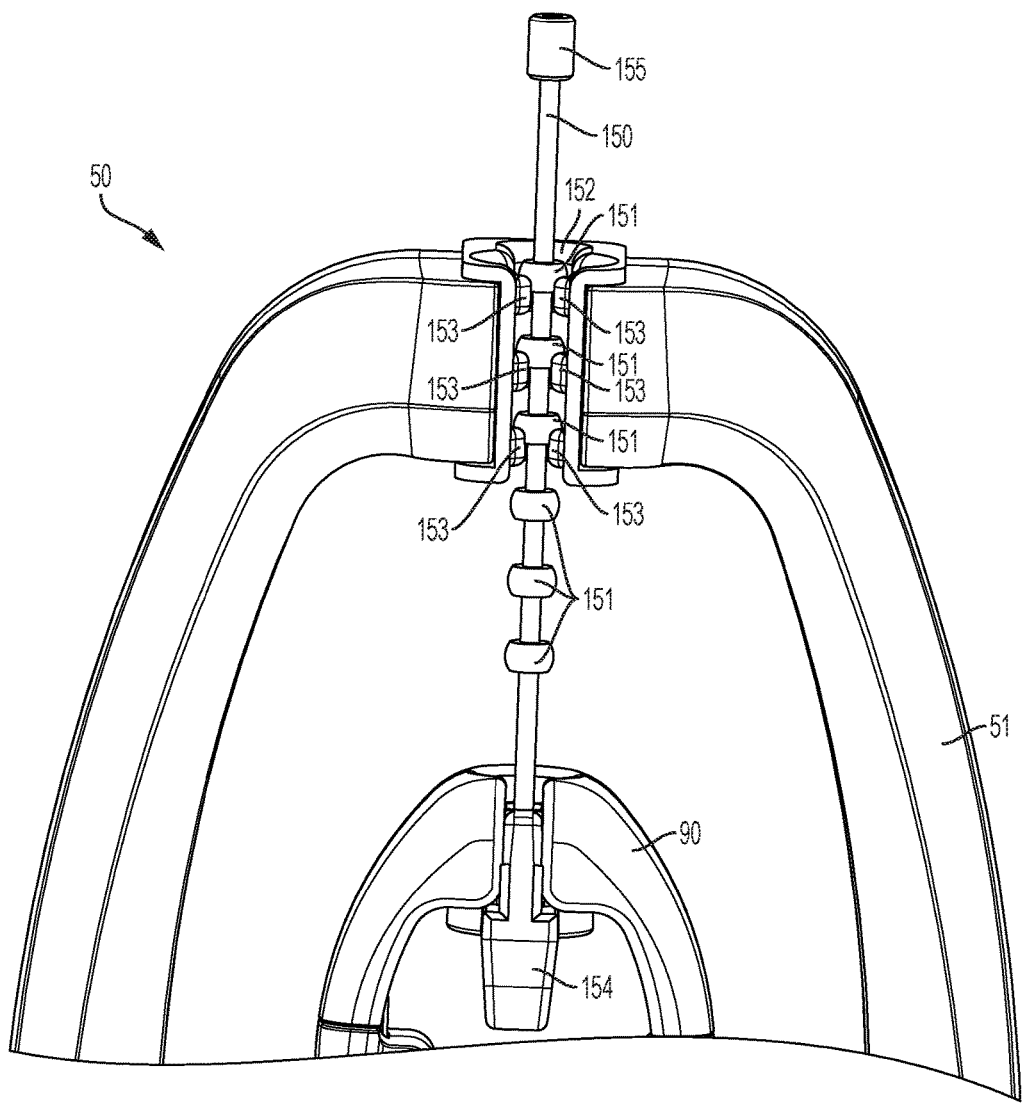
FIG. 11 is a close-up view of the catch assembly and positioning cable of the appliance shown in FIG. 10.
Figure 12:
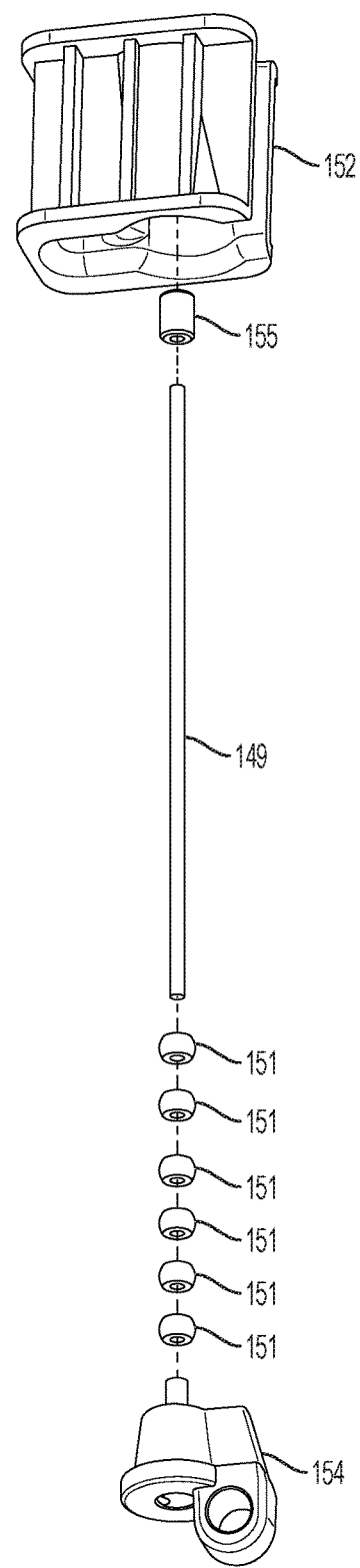
FIG. 12 is an exploded view of the catch assembly and positioning cable of the appliance in FIG. 10.
Figure 13:
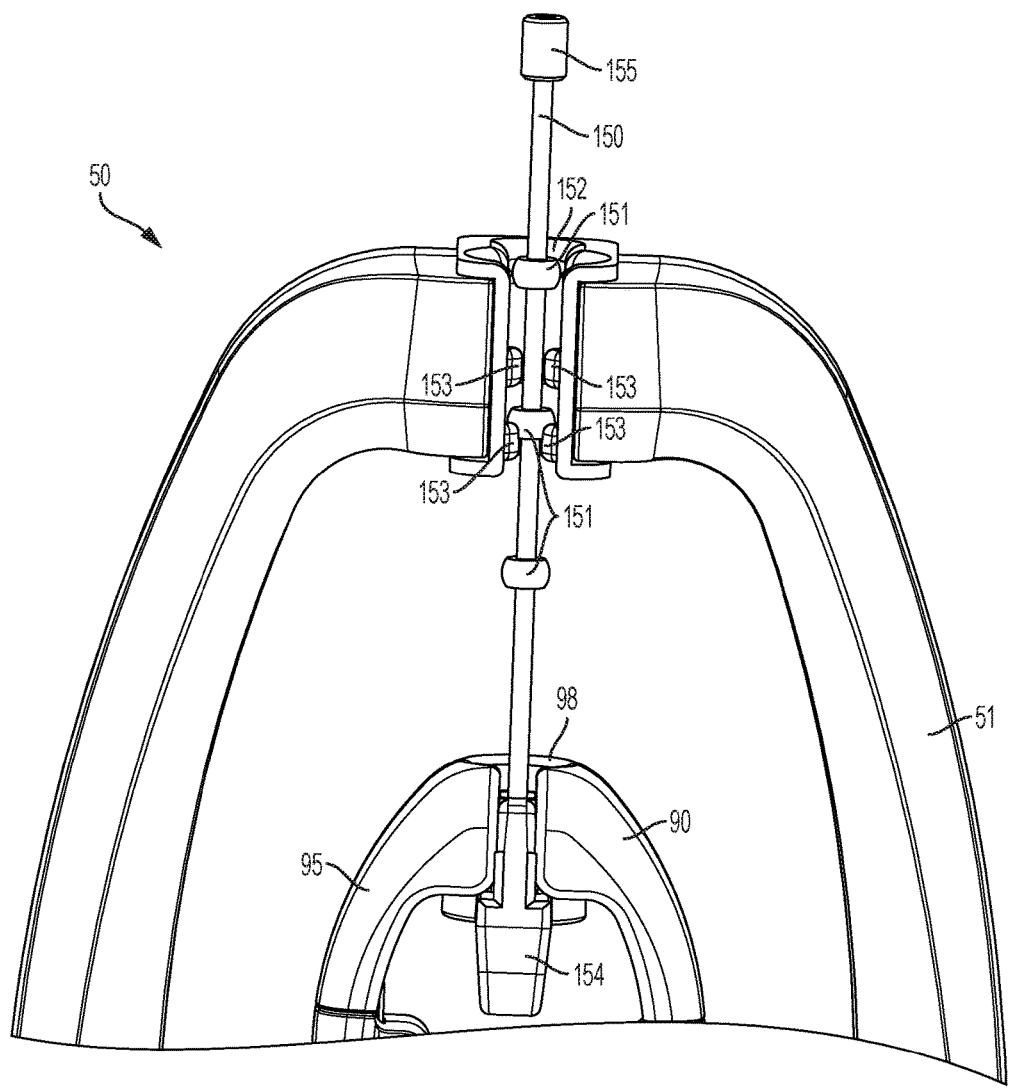
FIG. 13 is an isometric view of the catch assembly and positioning cable of an alternative embodiment of an appliance in accordance with the invention.

FIGS. 10-13 show an alternative embodiment of an appliance 50 in accordance with the invention, configured for hand strength assessments. In this embodiment, appliance 50 includes a frame 51, having a handle end 52 and a connector end 53, as well as a channel 55 on the interior surface 65 of the frame 51. Appliance 50 also includes an internal handle 54 that is slidable within the channel 55. The internal handle 54 includes a bar 57, sliding portions 59 and a stabilizing member 58 that includes a stabilizing socket 67. But the internal handle 54 shown in this embodiment does not have niches 60; rather, the adjustability of various positions is accomplished in a different way and by inserting a force sensing device 90 in a different orientation. As shown in FIG. 10, the neck 92 of a force sensing device 90 is inserted in the stabilizing socket 67 and has a tight fit with plug 93 when in use In this embodiment, the appliance 50 is used with a positioning cable 150 having multiple balls 151 that is positioned by using a catch assembly 152 within the connector socket 64. As shown in FIGS. 11 and 12, the positioning cable 150 has a positioning cable plug 154 at one end, and a positioning cable cap 155 at the other end. The positioning cable plug 154 is securely inserted within the socket passage 98 of the force sensing device 90. As shown in FIG. 10, the force sensing device 90 may itself be securely inserted within the stabilizing socket 67 of the stabilizing member 58 of the internal handle 54. A force sensing device 90 may of course have a variety of configurations or shapes. As shown in FIG. 10 and FIG. 10A, the force sensing device 90 is part of a force sensor assembly 85, which includes a force sensing device 90 as well as a positioning cable 150, which in this embodiment works with catch assembly to secure the force sensor assembly 85 within the appliance 50. When securely inserted in the internal handle 54, the plug 93 of the force sensing device 90 is tightly fit against the outer stabilizing socket end 68, with the neck 92 nestled within the stabilizing socket 67 and extending through the inner stabilizing socket end 69. In this embodiment, the force sensing device 90 may be used not only with the positioning cable 150 but also with resistance bands, elastic cables, or other insertable exercise devices that are capable of being engaged within the socket passage 98 of the force sensing device 90. A force sensor assembly 85 or the combination of a force sensing device 90 with other elements may comprise a resistance element that can be used in this embodiment. Other types of resistance elements may be used in other embodiments of an appliance 50, As shown in the drawings, adjusting the position of the stabilizing member 58 in an appliance 50 using a positioning cable 150 is accomplished by re-positioning the positioning cable within the catch assembly 152 to adjust the distance between the bar 57 and handle end 52. Catch assembly 152 contains multiple stops, which correspond with positions for the bar 57 relative to the handle end 52. Catch assembly 152 may be removable or fixed, depending on the embodiment. As shown in FIGS. 11 and 12, the positioning cable 150 has six balls 151 and the catch assembly 152 has six stops 153 (three on each side) that provide for six different positions. FIG. 13 shows an alternative embodiment of positioning cable 150 and catch assembly 152, where the positioning cable 150 has three balls 151 and four stops 153 (two on each side) for two different positions, by which the user may achieve six different bar 57 positions altogether.

Figure 14:
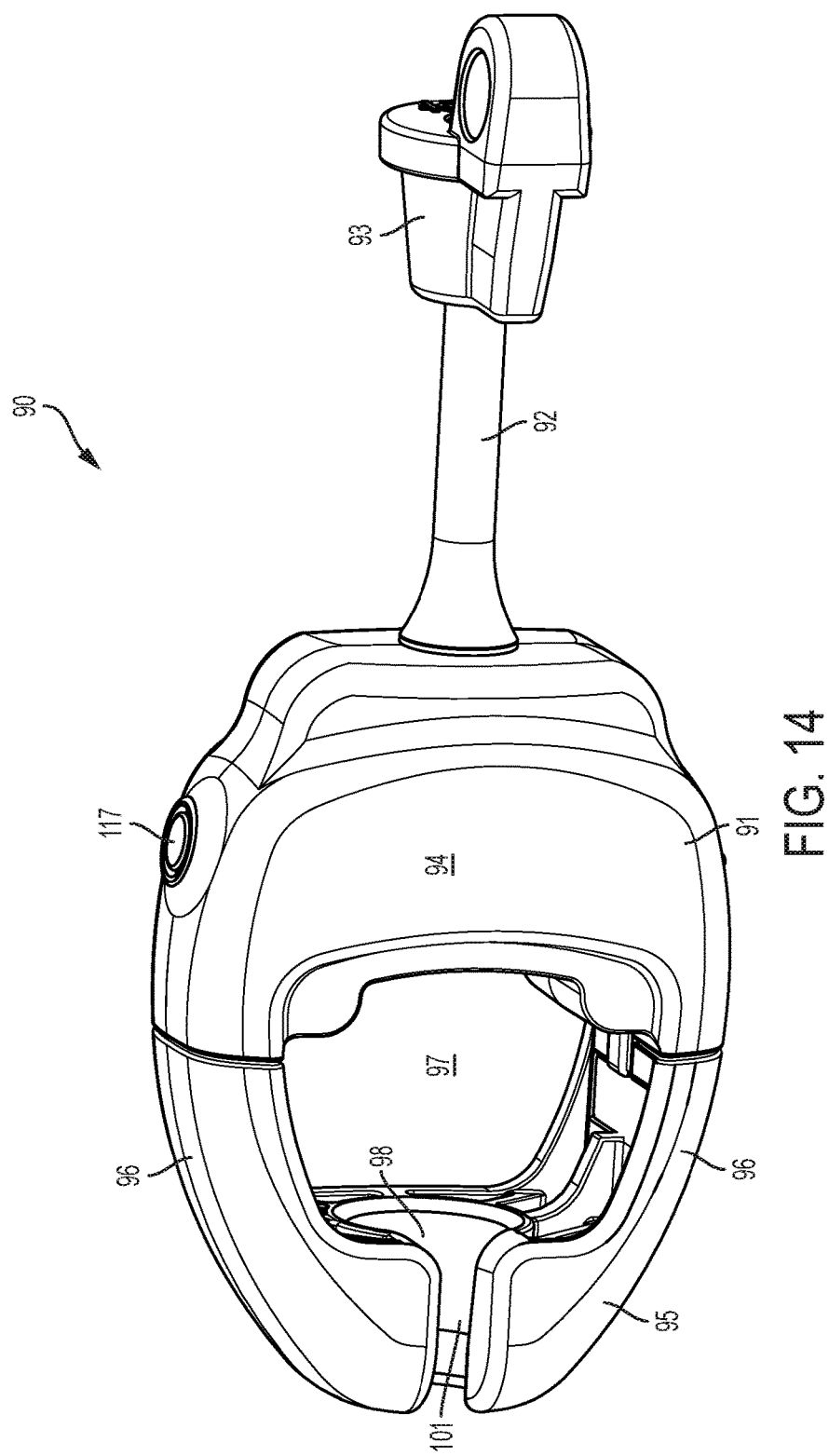
FIG. 14 is an isometric view of a force sensing device that maybe used with the appliance in accordance with the invention.

A force sensor and wireless transmitter can be used to measure force in the appliance 50 and wirelessly transmit information to computer about that force and the exercises or reps performed. Force sensors that could be used with the appliance 50 are also described in U.S. Pat. No. 8,491,446 and U.S. Application Publication No. 2014/0323271, which are incorporated here by reference for all purposes. FIG. 14 shows an example of a force sensing device 90 that may be used with an appliance 50 in accordance with the invention. Force sensing device 90 may include a body 91 consisting of a base section 94 and a socket section 95. Body 91 may include a force sensor 111 or load cell such that tension between the base section 94 and the socket section 95 and thus on the force sensor 111 therein, results in a measurable signal, thus resulting in test position data or exercise data, representative of the force between the base section 94 and the socket section 95. Base section 94 may also be connected to a neck 92 having a plug 93.

Socket section 95 includes a pair of socket section sides 96 spaced by a body passage 97 extending between opposite socket section sides 96. Socket section 95 also includes a socket passage 98, which extends between an inner socket passage end 99 opening into the body passage 97, and an opposing outer socket passage end 100. The socket section 95 of the body 91 has a slot 101 opening into the socket passage 98, which effectively defines a pocket for receiving a connector 102). The slot 101 is preferably sized such that connectors 102, such as the connectors of an elastic member, resistance band, or anchor for testing (e.g. a positioning cable 150 or anchoring insert 120), cannot pass through the slot. For example, an elastic member or resistance cable (e.g., 140, 141, 144), 105 having a stabilizing end 142 can then be easily installed into the socket passage 98 by situating the stabilizing end in the body passage 97, and then pulling the length of the elastic member or resistance cable along the slot 101 (while holding the stabilizing end 142 within the body passage 97), such that the length of the cable or member (whose diameter decreases with elongation) can fit through the slot 101 and into the socket passage 98. The elastic member, resistance cable, or other insert can then be released to fit securely for use within the socket passage 98.

Figure 15:
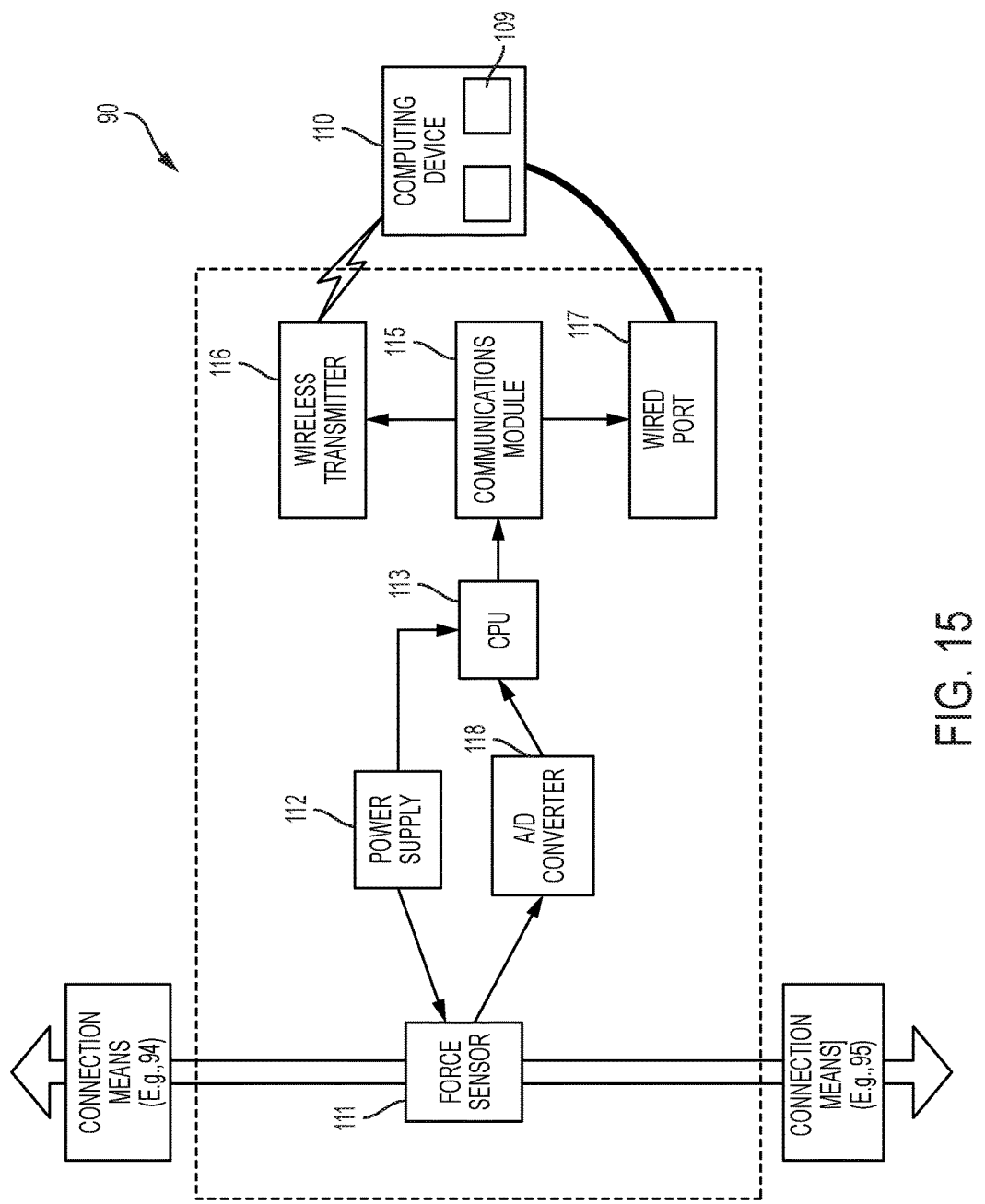
FIG. 15 is a schematic drawing illustrating the key internal components of a force sensing device and its interaction with a computing device.

FIG. 15 is a schematic drawing illustrating the key internal components of the force sensing device 90 and its interaction with a computing device 110. The force sensor(s) 111 is supplied with an input voltage from the power supply 112, and generates an output voltage dependent on the input voltage and on any force exerted on the connection means e.g., the base section 94 and socket section 95 of the body 91 of the force sensing device 90) The output voltage is supplied to the analog to digital converter (converter 118), which converts the output voltage into digital form and supplies it to the processor (CPU 113). The CPU 113 converts the output voltage from the force sensor 111 into a force measurement, and may also perform additional processing steps, e.g., breaking the force readings into time-stamped packets, manipulating the force readings (e.g., integrating them over time to obtain power measurements), storing a history of force readings onto an on-board memory (not shown) and performing analyses on recorded readings (related to, for example, progress over time), etc. The resulting data is then provided from the CPU 113 to the communications module 115, which translates the data into a transmittable signal for communication to a computing device 110 via a wireless transmitter 116 and/or via a wired port 117. Data transmitted may include test position data from various grip or pinch strength testing positions or may include exercise data from different exercises or exercise routines. Computing device 110 may include traditional desktop or laptop computers, as well as tablets and smart-phones, or any other computing device. Software used by or stored on computing device 110 may also provide instructions for storing data, analyzing data, and performing analyses, for example as described in U.S. Published App. No. 2014/0205980.

Grip Assessment Configurations

FIGS. 16-20 are a sequence of drawings that illustrate an appliance 50 positioned in several different grip assessment positions. As shown in the figures, a force sensing device 90 is inserted into the frame 51 of an appliance 50. As shown in FIG. 16A, the force sensor assembly 85 includes a force sensing device 90 and an anchoring insert 120, which anchors the force sensing device 90 within the appliance 50. Anchoring insert 120 may include an anchoring connector 121, anchoring shaft 122, and anchoring base 123. As shown in FIGS. 16-20, the anchoring connector 121 may be fit within the socket passage 98 of the force sensing device 90. For grip strength testing, anchoring insert 120 or positioning cable 150 should be made of a rigid material. By way of example; a positioning cable 150 may be made from a stainless-steel cable with stainless-steel balls 151 swaged onto the cable in the desired positions. On the other end of the anchoring insert 120, the anchoring shaft 122 and anchoring base 123 are fit within the stabilizing socket 67 on the stabilizing member 58 of the internal handle 54.

The force sensing device 90 is inserted into the appliance 50 by placing the neck 92 of the force sensing device 90 in the connector socket 64 of the connector end 53 of the appliance 50. The neck 92 of the force sensing device 90 is inserted into the connector socket 64 and the plug 93 is secured with a tight fit resulting from the combination of force sensing device 90 and anchoring insert 120. The use of the anchoring insert 120 forms a rigid connection between the force sensing device 90 and appliance 50, enabling isometric assessment. In this configuration, the handle no longer is moveable; it is fixed in position according to the location of the stabilizing member 58. In this configuration the appliance 50 is well suited to serve the purpose of being a grip strength assessment tool.

Figure 16:
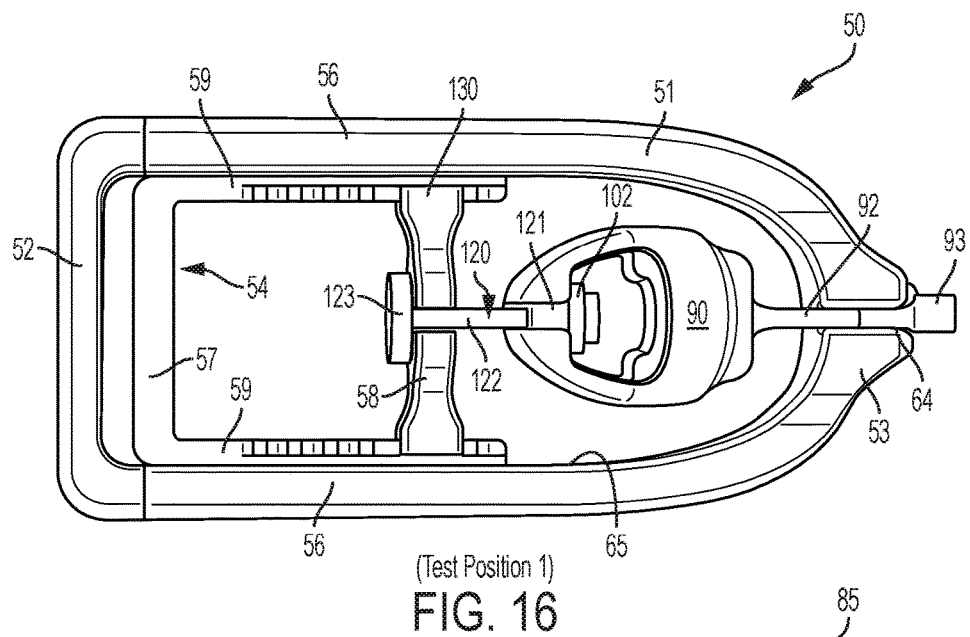
FIG. 16 is an elevation view of an appliance in accordance with the invention showing the appliance set for a first test position.
Figure 16A:
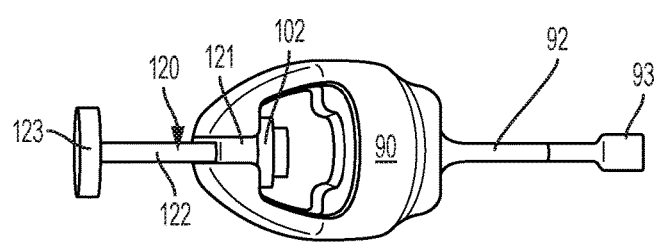
FIG. 16A is an elevation view of an alternative embodiment of a force sensor assembly, also shown in the appliance in FIG. 16.
Figure 17:
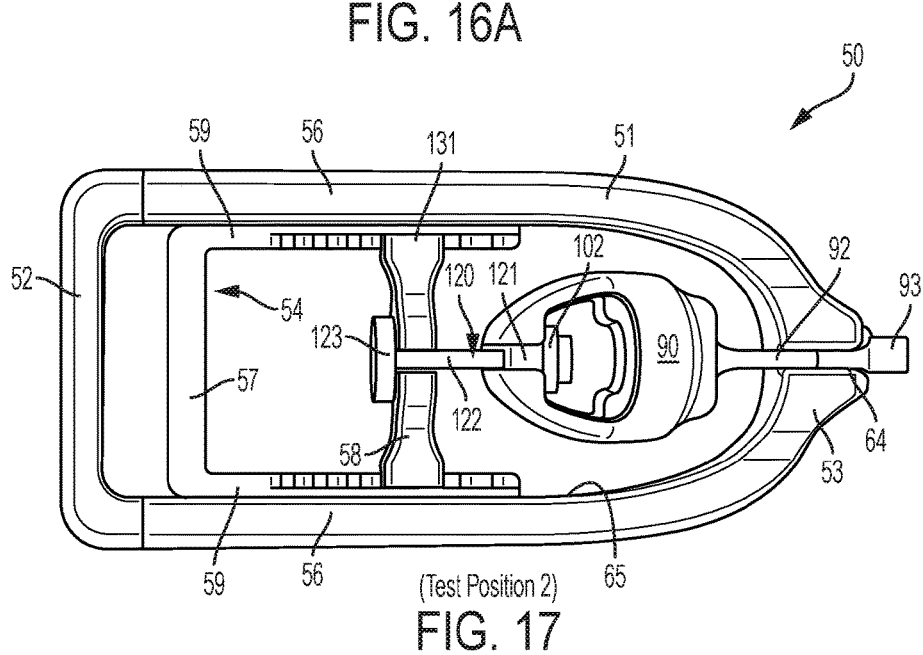
FIG. 17 is an elevation view of the appliance in FIG. 16 showing the appliance set for a second test position.
Figure 18:
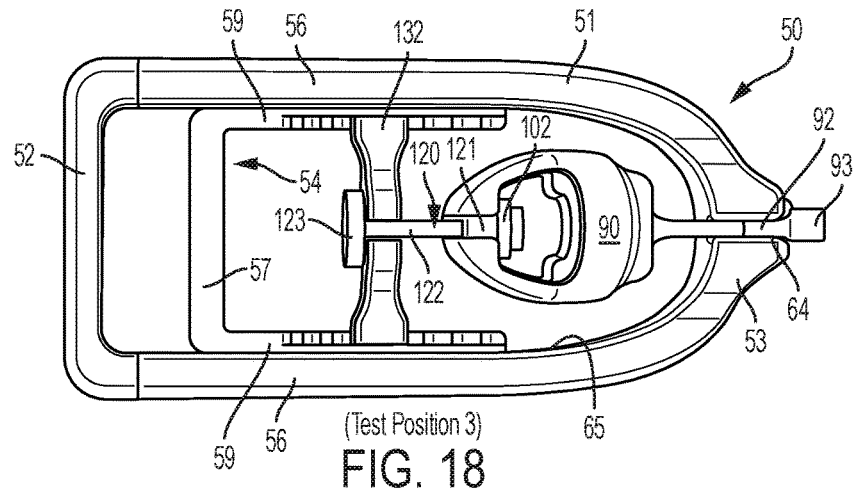
FIG. 18 is an elevation view of the appliance in FIG. 16 showing the appliance set for a third test position.
Figure 19:
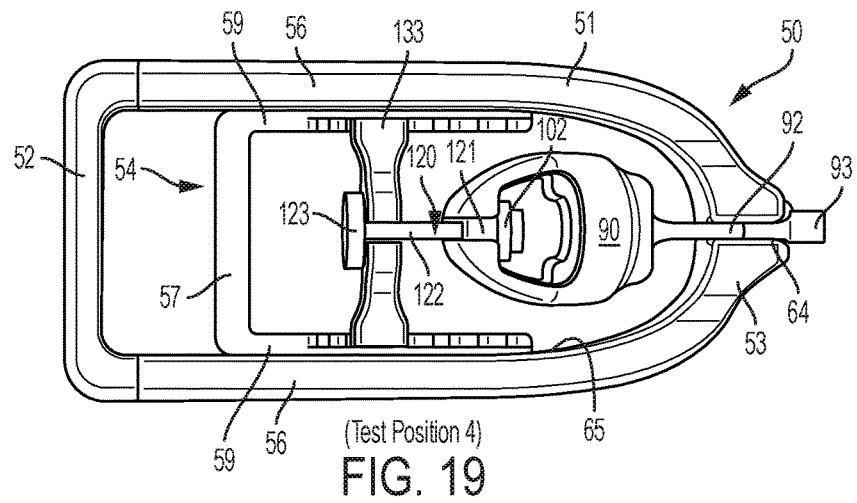
FIG. 19 is an elevation view of the appliance in FIG. 16 showing the appliance set for a fourth test position.
Figure 20:
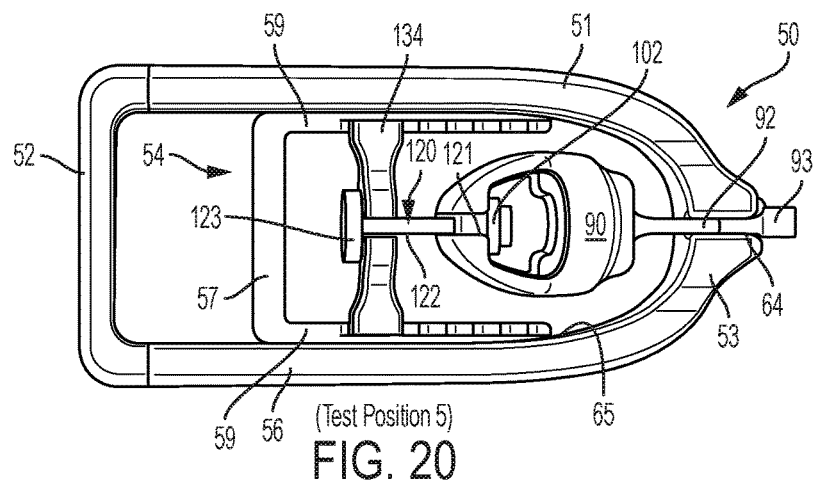
FIG. 20 is an elevation view of the appliance in FIG. 16 showing the appliance set for a fifth test position.

FIGS. 16-20 show how the position of the stabilizing member 58 with respect to the internal handle 54 provides multiple test positions for evaluating grip strength. These figures show five different grip strength test positions because there are five positions commonly used during such testing today, but an appliance 50 with more or less testing positions would also fall within the scope of the invention. To adjust the appliance 50 for different test positions, the stabilizing member 58 is removed from the internal handle 54 and replaced into the desired niches 60 corresponding with the desired test position (as illustrated in FIG. 9A). Accordingly, FIG. 16 shows stabilizing member 58 at a first test position 130. FIG. 17 shows stabilizing member 58 at a second test position 131. FIG. 18 shows stabilizing member 58 at a third test position 132. FIG. 19 shows stabilizing member 58 at a fourth test position 133. FIG. 20 shows stabilizing member 58 at a fifth test position 134.

FIGS. 26 through 31 show how an alternative embodiment of an appliance 50 may be positioned to achieve five different grip strength test positions and one pinch test position using a positioning cable 150. Different combinations of balls 151 and stops 153 may be used within the spirit of the invention. Different mechanical means for positioning the stabilizing member 58 may also be used that will be apparent to one of skill in the art that are not described here, but which fall within the scope of the invention.

To measure grip strength, the user grips the appliance 50 with the palm of the hand grasping the handle end 52, and the user will squeeze the bar 57 of the internal handle 54 towards the handle end 52 of the appliance 50. Pinch strength is measured similarly, but will use one or more fingers to squeeze the bar 57, depending on the pinch test position being used. The squeezing of the bar 57 produces an isometric force which the force sensor(s) 111 within the force sensing device 90 can measure and transmit to a receiving computing device 110 (e.g., PC, tablet, smart-phone, etc.) running corresponding assessment software. A therapist or coach performing the assessment n quickly change the test position from "1" through "5" in order to collect the grip strength data desired. Again, multiple configurations, positions or number of positions could be used within the spirit of the invention. Furthermore, as shown in the various drawings, the frame 51 may be designed in such a shape that the frame 51 may be rested on a table or surface and be self-standing, that is, "stand-up" on its own so that the appliance 50 may be used for assessments for individuals who may not be strong enough to hold the appliance 50 on their own, or for use without the aid of a coach or therapist.

Figure 22:
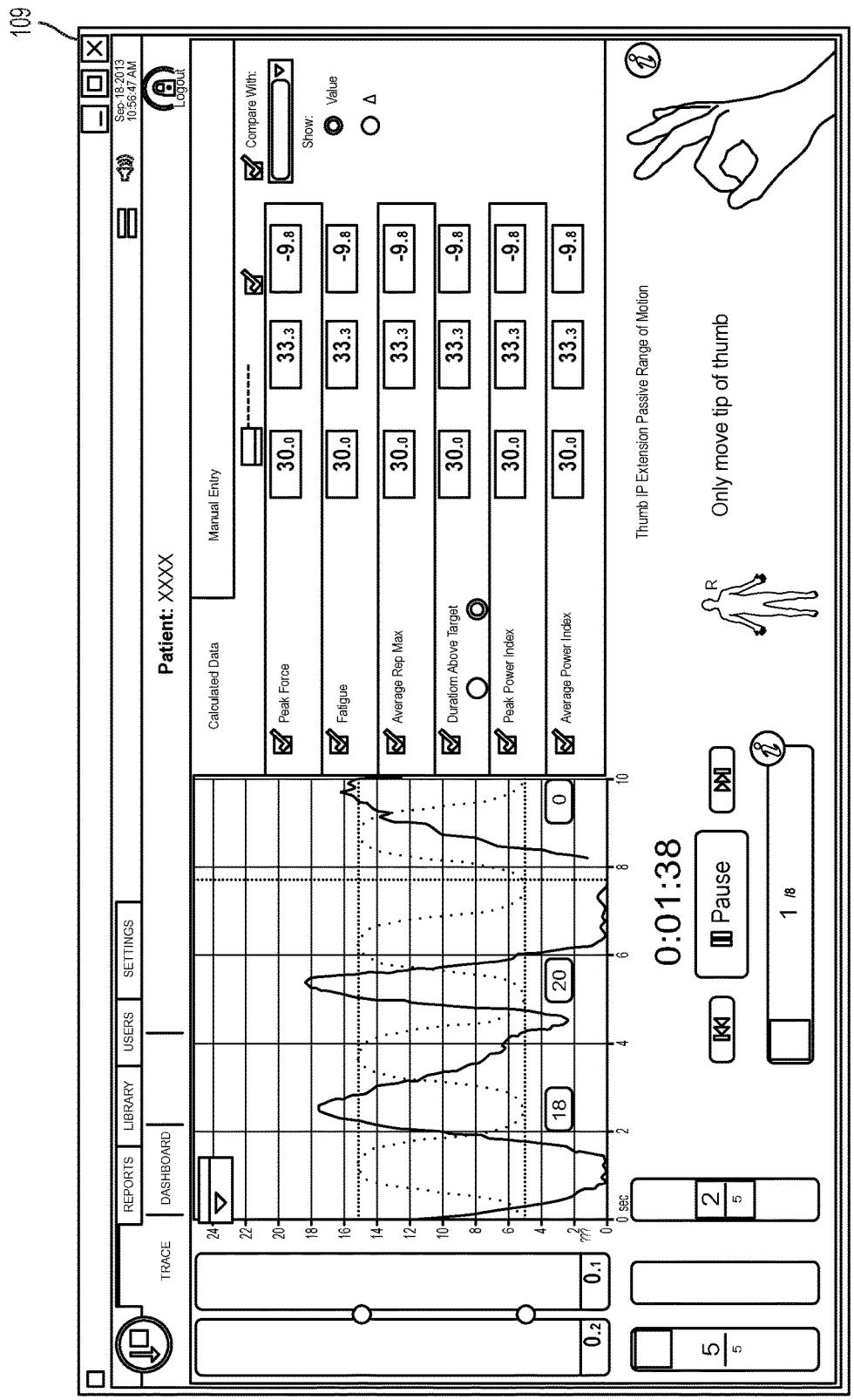
FIG. 22 is a view of a display interface, showing how an appliance in accordance with the invention may be used in an exercise system including a computing device to track and collect data regarding exercises performed using the appliance.

The appliance 50 has several advantages over existing hand strength assessors. When used with a force sensing device 90, an appliance 50 in accordance with the invention can be used to provide continuous and real-time data, providing useful feedback to the patient, therapist, athlete, coach, or others. :Feedback can be provided on a display interface 109 of a computing device 110 or by way of indicators, such as illuminated bars, on the force sensing device 90 itself. FIG. 22 shows an example of a display interface 109 showing assessment data being tracked in real time using accompanying software. A display interface 109 and accompanying software may also be used to collect data regarding exercises performed using the appliance 50 and to store data from both testing and exercise, thus allowing the force sensing device 90 to be used to track progress towards goals or to provide data back to a therapist or coach. As shown in FIG. 22, data displayed and tracked may include, but is not limited to, peak force, average force, work, fatigue, power, time held above target, average power, coefficient of variable, etc., so performance data may be viewed as it occurs. Alternatively, or in addition, data can be downloaded or saved for later use. The appliance 50 may also be easily adjusted to provide multiple test positions by adjusting the position of the bar 57 relative to the handle end 52. The appliance 50 may be positioned easily at different angles to test differences in hand strength when the hand and forearm are level with the ground, perpendicular to the ground (90° angle), or any other angle, hand, or arm position. Additionally, the appliance 50 will enable therapists and coaches to easily test hand strength one hand at a time, as well as when the user switches hands back and forth quickly between the right and left hands. Software used with an appliance 50 and force sensing device 90 may also accommodate and provide a mode for operation in which the user (e.g. patient or athlete) is rapidly switching between left hand and right hand use, or is rapidly switching between different pinch positions, for either assessment or exercise purposes, and for providing live or real-time feedback and automatic calculations for this type of use.

Pinch Assessment Configurations

Figure 21:
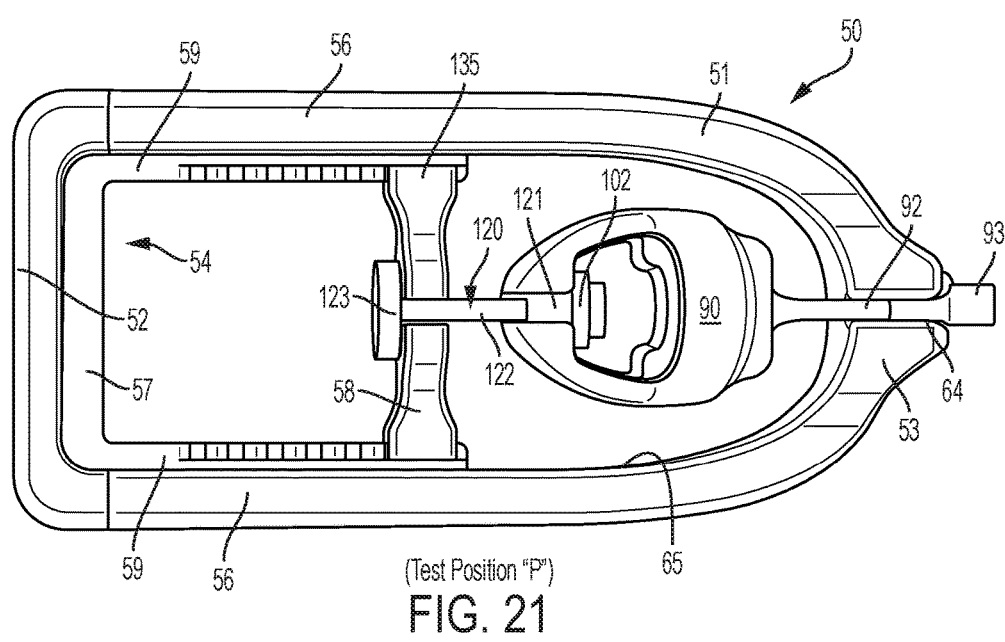
FIG. 21 is an elevation view of the appliance in FIG. 16 showing the appliance set for a pinch test position.

In addition to assessing grip strength, the appliance 50 can also be used in a configuration to assess or test pinch strength. FIG. 21 shows an appliance 50 configured with the stabilizing member 58 set at a pinch test position 135, in which the stabilizing member 58 was adjusted as described above. In the pinch test position 135, this will typically be the position in which there is the shortest gap between the handle end 52 of the appliance 50 and the bar 57 of the internal handle 54. The internal portion of the handle end 52 of the appliance 50 may include a recess such that there is a small space between the end of the bar 57 and the internal surface of the handle end 52 of the appliance 50, even though there may be no gap between these two surfaces when viewed in the orientation shown in FIG. 21. Multiple pinch positions can be accommodated with this design, including but not limited to, such standard positions as Palmar (pinch between the tips of fingers pressed against palm of the hand), Key (in which the thumb is opposed to the middle phalanx of the index finger), and Tip (in which the tip of the thumb is pressed against any, all, or each of the tips of the fingers). Results and data generated by the force sensing device 90 in connection with pinch testing may also be viewed and tracked using a computing device 110 and display interface 109, as shown in FIGS. 15 and 22, FIG. 26 shows an alternative embodiment of an appliance 50 configured for a pinch test position.

Exerciser Configurations

Figure 23:
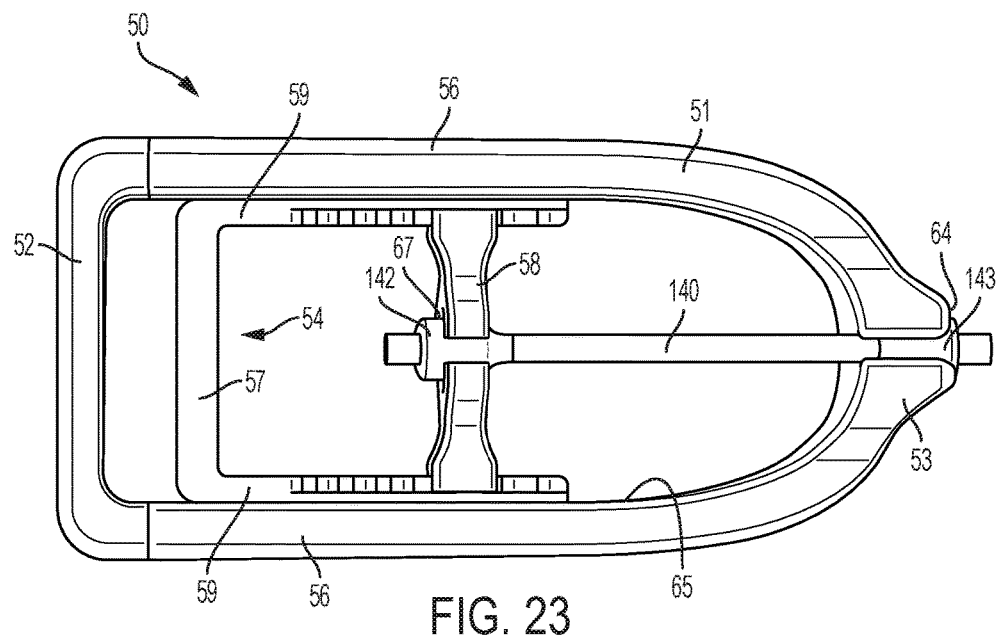
FIG. 23 is an elevation view of an appliance in accordance with the invention, showing the appliance configured for exercise with a first resistance cable.

An appliance 50 in accordance with the invention may also be used as an exercise device for performing exercises to increase hand strength (both grip and pinch strength). One configuration in which an appliance 50 may be used as an exerciser is in connection with resistance cables, elastic cables, stretchable bands, or other exercise devices. FIG. 23 shows an appliance 50 with a resistance cable 140 positioned within the frame 51. As shown in the figure, a first resistance cable 140 has a stabilizing end 142 and a connector end 143 and is secured within the appliance 50 by securing stabilizing end 142 within the stabilizing socket 67 of the stabilizing member 58 and by securing connector end 143 within the connector socket 64 of the frame 51. Unlike the previously described configuration for assessment, which used a rigid connector 121 for isometric testing, this configuration allows the internal handle 54 to move in a sliding fashion back and forth within the channel 55, thus stretching and relaxing the cable this configuration, the appliance 50 serves as an exercise device. The appliance 50 may be designed to work with cables and connectors of existing systems, such as those using a slotted-pocket quick connect system disclosed in U.S. Pat. Nos. 6,923,750 and 6,497,641, which are incorporated herein by reference.

Figure 24:
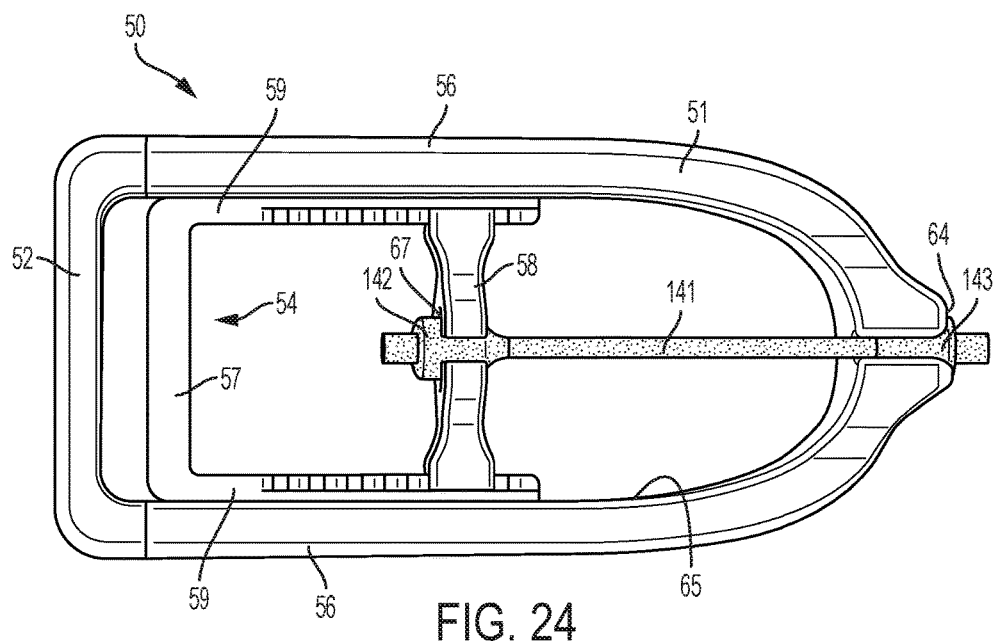
FIG. 24 is an elevation view of the appliance of FIG. 18, showing the appliance configured for exercise with a second resistance cable.

The appliance 50 is designed for quick cable interchange as well, such that the user can swap out the cable for other cables of varying resistance levels. For example, the user could insert a resistance cable for levels less than 10 lbs, or they could insert a more rigid cable to achieve resistance in excess of 50 lbs. While FIG. 23 shows the use of a first resistance cable 140. FIG. 24 shows an example of the appliance 50 used with a second resistance cable 141 providing a different level of resistance.

When the appliance 50 is used as an exercisor, the amount of stretch imparted on the cable in the starting exercise position can be increased or decreased (and thus difficulty of the exercise easily increased or decreased) by changing the position of the stabilizing member 58 within the internal handle 54. Effort can also be adjusted by using cables of different lengths, in which a shorter cable would require a greater force throughout the given motion or exercise. The combination of changing cables along with changing the starting position of the stabilizing member 58 provides for many variations in workout configurations.

Tracking Configurations

Figure 25:
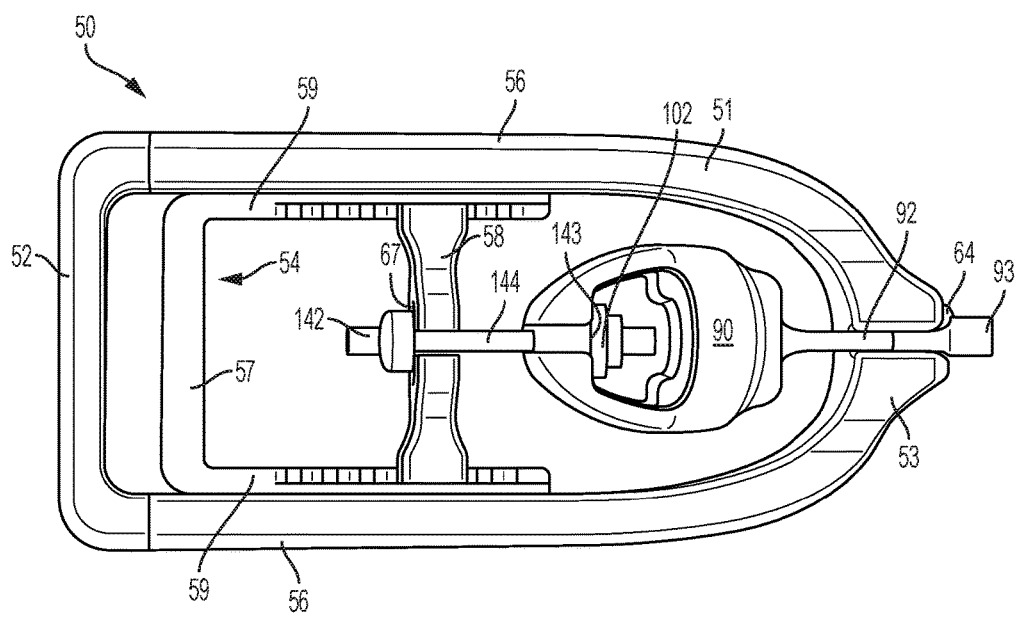
FIG. 25 is an elevation view of an appliance in accordance with the present invention, being used with a short resistance cable and a force sensing device.

Yet another configuration for the appliance 50 is to use a force sensing device 90 in combination with a short resistance cable 144 inserted in the appliance 50 as shown in FIG. 25 to achieve both an exercise function and an exercise tracking function. In this configuration, the internal handle 54 is free to slide back and forth to stretch and relax the cable while the force sensing device 90 tracks the effect and communicates exercise data to a computing device 110. This configuration thus permits monitoring of a user's progress throughout an exercise session as well as through an exercise program (consisting of multiple sessions).

Another advantage of the inventions disclosed and claimed here is that an appliance 50 can be used with a force sensing device 90 to track data from various exercises performed with the appliance 50, and the same force sensing device 90 may be used with other exercise equipment for tracking purposes to provide an integrated exercise system. For example, a force sensing device 90 can be used with mountable exercise apparatus as described in U.S. Application Pub. No. 2015/0133278 or with resistance cables and exercise handgrips as identified in U.S. Pat. Nos. 8,491,466 and 6,923,750, as well as with an appliance 50 as described here. A force sensing device 90 may be used in connection with exercises or testing for arms, legs, core, and other areas. When used in this manner, the force sensing device 90 may be used not only with hand strength exercises or testing, but for a whole body workout, exercises, or testing.

Although the invention has been herein described in what is perceived to be the most practical and preferred embodiments, it is to be understood that the invention is not intended to be limited to the specific embodiments set forth above. Rather, it is recognized that modifications may be made by one of skill in the art of the invention without departing from the spirit or intent of the invention and, therefore, the invention is to be taken as including all reasonable equivalents to the subject matter of the appended claims and the description of the invention herein.

What is claimed is:

1. A multiple configuration hand assessment and exercising appliance comprising:
   a frame having a connector end with a connector socket, a handle end, and a channel on an interior surface of the frame;
   an internal handle having a bar and two sliding portions, the internal handle fitted within the frame and slidable within the channel:
   a stabilizing member adjustably connected to the two sliding portions, the stabilizing member including a stabilizing socket for positioning the bar with respect to the handle end of the frame to provide multiple test positions; and
   a force sensor assembly secured within the connector socket on the connector end of the frame and within the stabilizing socket, the force sensor assembly capable of processing and transmitting force measurement data to a computing device.

2. The appliance of claim 1, wherein the force sensor assembly further comprises a force sensing device including a body having a neck, a base section, a socket section, and a force sensor within the body, such that the force sensor is capable of measuring tension between the base section and the socket section when force is exerted on the socket section, resulting in a measurable force signal.

3. The appliance of claim 2, wherein the force sensor assembly further includes an anchoring insert, the anchoring insert comprising:
   an anchoring connector removably secured within a socket passage of the force sensing device, an anchoring base removably secured within the stabilizing socket of the stabilizing member, and an anchoring shaft; and wherein the neck of the force sensing device is secured within the connector socket and wherein the anchoring base is secured within the stabilizing socket.

4. The appliance of claim 3, wherein the stabilizing member is capable of being positioned in five different grip test positions.

5. The appliance of claim 4 wherein the stabilizing member is capable of being positioned in a pinch test position.

6. The appliance of claim 2, wherein the force sensor assembly further comprises:
   a positioning cable having a length and having a positioning cable plug that may be removably secured within a socket passage of the force sensing device;
   multiple balls on the length of the positioning cable;
   a catch assembly that may be removably secured within the connector end of the frame, the catch assembly having stops that provide positions for securing one or more balls on the positioning cable and thus adjustment of the positioning cable and thus the positions of the balls within the catch assembly provides multiple test positions for the appliance.

7. The appliance of claim 6, wherein the stabilizing member may be positioned in five different grip test positions by positioning the balls of the positioning cable in different positions within the catch assembly.

8. The appliance of claim 7 wherein the stabilizing member may additionally be positioned in a pinch test position.

9. The appliance of claim 1, wherein the appliance is used for exercise and the force sensor assembly further comprises a resistance cable having a stabilizing end and a connector end, the stabilizing end removably secured within the stabilizing socket and the connector end removably secured within a socket passage of a force sensing device having a neck removably secured within the connector socket of the frame.

10. The appliance of claim 1, wherein the force sensor assembly is capable of being used in connection with additional exercise devices.

11. A hand strength appliance comprising:
    a frame having arms; a handle end, an interior surface, and a connector end including a connector socket;
    an internal handle fitted within the frame and slidable within an interior surface of the frame, the internal handle including a bar and two sliding portions that are operably connected to the bar and together slide within the interior surface of the frame; and
    a stabilizing member adjustably connected to the two sliding portions, the stabilizing member including a stabilizing socket for positioning the bar with respect to the handle end of the frame to provide multiple test positions;
    the appliance capable of receiving and securing one or more removable resistance elements within the connector socket and the stabilizing socket.

12. The appliance of claim 11, further comprising a resistance element that is an anchoring insert comprising:
    an anchoring connector removably secured within a socket passage of a force sensing device, an anchoring base removably secured within the stabilizing socket of the stabilizing member, and an anchoring shaft; and wherein a neck of the force sensing device is secured within the connector socket and wherein the anchoring base is secured within the stabilizing socket;
    and wherein the appliance is configured for hand strength assessment.

13. The appliance of claim 12, further comprising a second resistance element that is a resistance cable and wherein the appliance is configured for hand strength exercise.

14. The appliance of claim 11, further comprising a resistance element that is a positioning cable assembly comprising:
    a positioning cable having a length and having a positioning cable plug that may be removably secured within a socket passage of a force sensing device;
    multiple balls on the length of the positioning cable;
    a catch assembly that is capable of being removably secured within the connector end of the frame, the catch assembly having stops that provide positions for securing one or more balls on the positioning cable, such that adjustment of the positions f the balls on the positioning cable within the catch assembly provides multiple test positions for the appliance;
    and wherein the appliance is configured for hand strength assessment.

15. The appliance of claim 14, further comprising a second resistance element that is a resistance cable and the appliance is configured for hand strength exercise.

16. The appliance of claim 11, further comprising a resistance element including a force sensing device.

17. The appliance of claim 11, wherein the frame is self-standing.

18. A method for assessing grip strength at multiple test positions comprising the steps of:
   providing an appliance set to a first test position, the appliance comprising:
      a frame having a connector end, a handle end, and a channel on an interior surface of the frame;
      an internal handle fitted within the frame and slidable within the channel, the internal handle including a bar operably connected to two sliding portions of the internal handle;
      a stabilizing member adjustably connected to the two sliding portions, the stabilizing member including a stabilizing socket for receiving a resistance element for positioning the bar with respect o the handle end of the frame to provide multiple test positions;
      a force sensor assembly secured within a connector socket on the connector end of the frame and within the stabilizing socket, the force sensor assembly capable of processing and transmitting force measurement data to a computing device;
   measuring isometric force from a user squeezing the bar towards the handle end of the appliance in the first test position, resulting in first test position data;
   adjusting the appliance by changing the position of the stabilizing member relative to the handle end of the frame to provide a second test position;
   measuring isometric force from the user squeezing the bar towards the handle end of the appliance in the second test position, resulting in second test position data; and
   communicating the first test position data and the second test position data to a computing device.

19. The method of claim 18, further comprising the step of providing the appliance for use for performing hand strengthening exercises.

20. The method of claim 18, further comprising the step of providing to a computing device real time data based on the measurement of isometric force from use of the appliance.

21. The method of claim 20, further comprising measuring the isometric forces while the user switches rapidly between the right and left hands for squeezing the bar towards the handle end of the appliance.

22. The method of claim 20 further comprising measuring the isometric forces while the user switches rapidly between different pinch test positions for squeezing the bar towards the handle end of the appliance.

* * * * *